(12) United States Patent
Kato et al.

(10) Patent No.: US 7,964,727 B2
(45) Date of Patent: Jun. 21, 2011

(54) QUINOLONECARBOXYLIC ACID COMPOUNDS HAVING 5-$HT_4$ RECEPTOR AGONISTIC ACTIVITY

(75) Inventors: Tomoki Kato, Chita-gun (JP); Kiyoshi Kawamura, Chita-gun (JP); Mikio Morita, Chita-gun (JP); Chikara Uchida, Chita-gun (JP)

(73) Assignee: Pfizer Inc., New York, NY (US)

( * ) Notice: Subject to any disclaimer, the term of this patent is extended or adjusted under 35 U.S.C. 154(b) by 1075 days.

(21) Appl. No.: 10/595,948

(22) PCT Filed: Nov. 10, 2004

(86) PCT No.: PCT/IB2004/003707
§ 371 (c)(1),
(2), (4) Date: May 22, 2006

(87) PCT Pub. No.: WO2005/049608
PCT Pub. Date: Jun. 2, 2005

(65) Prior Publication Data
US 2008/0255113 A1 Oct. 16, 2008

Related U.S. Application Data

(60) Provisional application No. 60/524,681, filed on Nov. 24, 2003.

(51) Int. Cl.
| | |
|---|---|
| C07D 221/02 | (2006.01) |
| C07D 215/00 | (2006.01) |
| C07D 413/00 | (2006.01) |
| A01N 43/40 | (2006.01) |
| A01N 43/42 | (2006.01) |
| A61K 31/435 | (2006.01) |
| A61K 31/44 | (2006.01) |

(52) U.S. Cl. ........ 546/112; 514/279; 514/277; 546/156; 544/128

(58) Field of Classification Search .................. 546/112, 546/156; 544/128; 514/277, 279
See application file for complete search history.

(56) References Cited

U.S. PATENT DOCUMENTS

| | | | | |
|---|---|---|---|---|
| 5,106,851 | A | 4/1992 | Turconi et al. | 514/259 |
| 5,248,684 | A | 9/1993 | Suzuki et al. | 514/299 |
| 5,571,820 | A | 11/1996 | Ohuchi et al. | 514/304 |
| 5,753,673 | A | 5/1998 | Ohuchi et al. | 514/304 |
| 6,544,997 | B1 | 4/2003 | Bosmans et al. | 514/255.05 |
| 6,951,867 | B2 * | 10/2005 | Katsu et al. | 514/300 |

FOREIGN PATENT DOCUMENTS

| | | | |
|---|---|---|---|
| EP | 0382687 | * | 8/1990 |
| JP | 0834783 | | 2/1996 |
| JP | 0834785 | | 2/1996 |
| JP | 09194374 | | 7/1997 |
| WO | WO9605166 | | 2/1996 |

OTHER PUBLICATIONS

Suzuki, M., Ohuchi, Y., Asanuma, H., Kaneko, T., Yokomori, S., Ito, C., Isobe, Y., Muramatsu, M. (2000) Synthesis and Evaluation of Novel 2-Oxo-1,2-dihydro-3-quinolinecarboxamide Derivatives as Serotonin t-HT4 Receptor Agonists. Chemical and Pharmaceutical Bulletin, vol. 48, No. 12, p. 2003-2008.*
Patent Abstracts of Japan, vol. 1996, No. 6, Jun. 28, 1996 (JP 08-034783).
Patent Abstracts of Japan, vol. 1996, No. 6, Jun. 28, 1996 (JP 08-034785).
Patent Abstracts of Japan, vol. 1997, No. 11, Jan. 28, 1997 (JP 09-194374).
English language abstract of WO 96/05166, Published Feb. 22, 1996.
Kishibayashi, N., et al., 5-HT3 Receptor Agonists. 3. Quinoline Derivatives Which May be Effective in the Therapy of Irritable Bowel Syndrome, vol. 36, No. 22, pp. 3286-3292, (1993).
International Search Report, mailed Mar. 10, 2005, PCT Appln. No. PCT/IB2004/003707.
International Preliminary Report on Patentability, dated Mar. 22, 2006, PCT Appln. No. PCT/IB2004/003707.

* cited by examiner

*Primary Examiner* — Shaojia Anna Jiang
*Assistant Examiner* — Scarlett Goon
(74) *Attorney, Agent, or Firm* — Jennifer A. Kispert; Richard V. Zanzalari

(57) ABSTRACT

This invention provides a compound of the formula (I): wherein Het represents a heterocyclic group having one nitrogen atom, to which B binds directly, and from 4 to 7 carbon atoms, and said heterocyclic group being unsubstituted or substituted by 1 to 4 substituents independently selected from the group consisting of substituents $\alpha^1$; A represents an alkylene group having from 1 to 4 carbon atoms; B represents a covalent bond or an alkylene group having from 1 to 5 carbon atoms; $R^1$ represents an isopropyl group, a n-propyl group or a cyclopentyl group; $R^2$ represents a methyl group, a fluorine atom or a chlorine atom; $R^3$ independently represents (i) an oxo group, a hydroxy group, an amino group, an alkylamino group or a carboxyl group; (ii) a cycloalkyl group having from 3 to 8 carbon atoms, and said cycloalkyl group being substituted by 1 to 5 substituents, or (iii) a heterocyclic group having from 3 to 8 atoms, and said heterocyclic group being unsubstituted or substituted by 1 to 5 substituents, and n is 1, 2 or 3, or a pharmaceutically acceptable salts thereof. These compounds have 5-$HT_4$ receptor agonistic activity, and thus are useful for the treatment of gastroesophageal reflux disease, non-ulcer dyspepsia, functional dyspepsia, irritable bowel syndrome or the like in mammalian, especially humans.

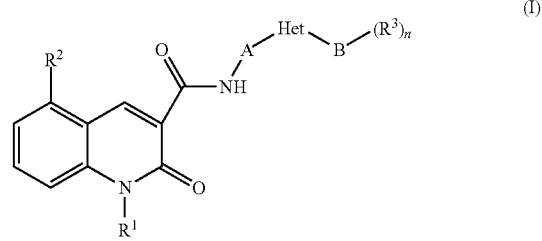

(I)

4 Claims, No Drawings

QUINOLONECARBOXYLIC ACID COMPOUNDS HAVING 5-HT₄ RECEPTOR AGONISTIC ACTIVITY

The present application is a national stage of PCT/220041003707 and claims priority of U.S. Appln. No. 60/524,681, filed 24 Nov. 2003.

TECHNICAL FIELD

This invention relates to novel quinolonecarboxylic acid compounds. These compounds have selective 5-HT$_4$ receptor agonistic activity. The present invention also relates to a pharmaceutical composition, a method of treatment and an use, comprising the above compounds for the treatment of disease conditions mediated by 5-HT$_4$ receptor activity.

BACKGROUND ART

In general, 5-HT$_4$ receptor agonists are found to be useful for the treatment of a variety of diseases such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, cardiovascular disorders such as cardiac failure and heart arrhythmia, and apnea syndrome (See TiPs, 1992, 13, 141; Ford A. P. D. W. et al., *Med. Res. Rev.*, 1993, 13, 633; Gullikson G. W. et al., *Drug Dev. Res.*, 1992, 26, 405; Richard M. Eglen et al., *TiPS*, 1995, 16, 391; Bockaert J. Et al., *CNS Drugs*, 1, 6; Romanelli M. N. et al., *Arzheim Forsch./Drug Res.*, 1993, 43, 913; Kaumann A. et al., *Naunyn-Schmiedeberg's*. 1991, 344, 150; and Romanelli M. N. et al., *Arzheim Forsch./Drug Res.*, 1993, 43, 913). Also, Mosapride is known to be useful for the treatment of diabetes. Further, Cisapride is known to be useful for the treatment of postoperative bowel motility (Tommy A. Brown et al., The American J. of Surgery, 177, p 399 (1999).

A variety of quinolonecarboxylic compounds as 5-HT$_4$ receptor agonists are disclosed by Taisho Co. Among them, a compound represented by the following formula is especially disclosed, which was selected as a preclinical compound TS-951 in Japanese Kokai Publication H09-194374:

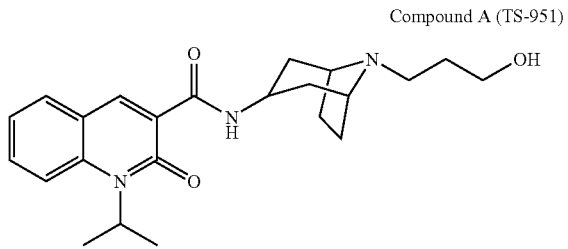

Compound A (TS-951)

BRIEF DISCLOSURE OF THE INVENTION

It has now surprisingly been found that quinolonecarboxylic compounds of this invention have a strong affinity to 5-HT$_4$ receptor by introducing a small size substituents such as a methyl group and a fluorine atom, and thus are useful for the treatment of disease conditions mediated by 5-HT$_4$ activity such as gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, and cardiovascular disorders such as cardiac failure and heart arrhythmia, diabetes, apnea syndrome (especially caused by an opioid administration), and postoperative bowel motility.

Further, the compounds of the present invention show a reduced QT prolongation by introducing a polar group into R$^3$ of the formula (I). QT prolongation is known to have a potential liability to produce fatal cardiac arrhythmias of Torsades de Pointes (TdP). The ability to prolong the cardiac action potential duration was identified as being due to an action at the HERG potassium channel. For example, drugs withdrawn from the market due to QT prolongation, such as Cisapride and Terfenadine, are known to be potent HERG potassium channel blocker (Expert Opinion of Pharmacotherapy.; 2, pp 947-973, 2000) Inhibitory activity at HERG channel was estimated from affinity for HERG type potassium channel was investigated by checking [³H]dofetilide binding, which can predict inhibitory activity at HERG channel (Eur. J. Pharmacol., 430, pp 147-148, 2001).

The compounds of the present invention may show a reduced QT prolongation, less toxicity, good absorption, distribution, good solubility, low protein binding affinity, less drug-drug interaction, and good metabolic stability.

The present invention provides a compound of the following formula (I):

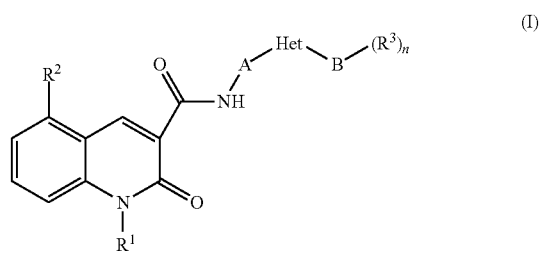

wherein

Het represents a heterocyclic group having one nitrogen atom, to which B binds directly, and from 4 to 7 carbon atoms, and said heterocyclic group being unsubstituted or substituted by 1 to 4 substituents independently selected from the group consisting of substituents α$^1$;

A represents an alkylene group having from 1 to 4 carbon atoms;

B represents a covalent bond or an alkylene group having from 1 to 5 carbon atoms;

R$^1$ represents an isopropyl group, a n-propyl group or a cyclopentyl group;

R$^2$ represents a methyl group, a fluorine atom or a chlorine atom;

R$^3$ independently represents
  (i) an oxo group, a hydroxy group, an amino group, an alkylamino group or a carboxyl group;
  (ii) a cycloalkyl group having from 3 to 8 carbon atoms, and said cycloalkyl group being substituted by 1 to 5 substituents independently selected from the group consisting of substituents α$^2$, or
  (iii) a heterocyclic group having from 3 to 8 atoms, and said heterocyclic group being unsubstituted or substituted by 1 to 5 substituents independently selected from the group consisting of substituents β, said substituents $\alpha^1$ are independently selected from a hydroxy group and an amino group;

said substituents $\alpha^2$ are independently selected from a hydroxy group, an amino group, a hydroxy-substituted alkyl group having from 1 to 4 carbon atoms, a carboxyl group and an alkoxy group having from 1 to 4 carbon atoms; and said substituents β are selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms and a carbamoyl group; and n is 1, 2 or 3, or a pharmaceutically acceptable salts thereof.

Also, the present invention provides a pharmaceutical composition for the treatment of disease conditions mediated by 5-$HT_4$ receptor, in a mammalian subject, which comprises administering to said subject a therapeutically effective amount of a compound of formula (I) or pharmaceutically acceptable salts thereof.

Further, the present invention also provides a pharmaceutical composition for the treatment of diseases selected from gastroesophageal reflux disease, gastrointestinal disease, gastric motility disorder, non-ulcer dyspepsia, functional dyspepsia, irritable bowel syndrome (IBS), constipation, dyspepsia, esophagitis, gastroesophageral disease, nausea, central nervous system disease, Alzheimer's disease, cognitive disorder, emesis, migraine, neurological disease, pain, and cardiovascular disorders such as cardiac failure and heart arrhythmia, diabetes and apnea syndrome, postoperative bowel motility, or the like, which comprises a therapeutically effective amount of the quinolonecarboxylic acid compound of formula (I) or its pharmaceutically acceptable salt together with a pharmaceutically acceptable carrier.

Also, the present invention provides a method for the treatment of disease conditions mediated by 5-$HT_4$ receptor, in a mammalian subject, which comprises administering to said subject a therapeutically effective amount of a compound of formula (I) or pharmaceutically acceptable salts thereof. Further, the present invention provides a method for the treatment of the disease conditions as mentioned above. Furthermore, the present invention provides use of the compound of formula (I) or pharmaceutically acceptable salts thereof in the manufacture of a medicament for the treatment of disease conditions mediated by 5-$HT_4$ receptor activity, in a mammalian subject. The conditions mediated by 5-$HT_4$ receptor activity include those diseases or disorders described as above.

DETAILED DESCRIPTION OF THE INVENTION

As used herein, the term "heterocyclic" of "Het" means a heterocyclic group having one nitrogen atom and from 4 to 7 carbon atoms such as

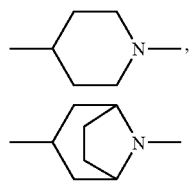 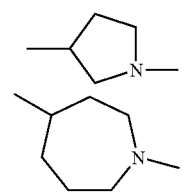 and

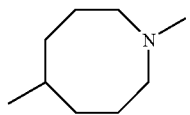

As used herein, the term "alkylene" in "A" means straight or branched chain saturated radicals having 1 to 4 carbon atoms, including, but not limited to methylene, ethylene, n-propylene, isopropylene, n-butylene, isobutylene, sec-butylene, tert-butylene. The "alkylene" in "A" represents preferably a methylene group, an ethylene group or a propylene group; more preferably a methylene group or an ethylene group; most preferably a methylene group.

As used herein, the term "alkylene" in "B" means straight or branched chain saturated radicals having 1 to 5 carbon atoms, including, but not limited to methylene, ethylene, n-propylene, isopropylene, n-butylene, isobutylene, sec-butylene, tert-butylene, n-pentylene, isopentylene, sec-pentylene, tert-pentylene. The "alkylene" in "B" represents preferably an alkylene group having from 1 to 4 carbon atoms; more preferably an alkylene group having from 1 to 3 carbon atoms; much more preferably a methylene group or an ethylene group; further more preferably a methylene group.

As used herein, the term "alkyl" of "an alkylamino" in "$R^3$"; "alkyl" of "a hydroxy-substituted alkyl group" and "an alkoxy group having from 1 to 4 carbon atoms" in "substituents $\alpha^2$"; "alkyl" in "substituents β"; and "alkyl" of "a hydroxy-substituted alkyl group" and "an amino-substituted alkyl group" in "substituents β" mean straight or branched chain saturated radicals having 1 to 4 carbon atoms, including, but not limited to methyl, ethyl, n-propyl, isopropyl, n-butyl, isobutyl, sec-butyl, tert-butyl.

As used herein, the term "cycloalkyl" in "$R^3$" means cyclic alkyl group having 3 to 8 carbon atoms, such as cyclopropyl, cyclobutyl, cyclopentyl, cyclohexyl, cycloheptyl, cyclooctyl, and etc.

As used herein, the term "heterocyclic" of "$R^3$" means a heterocyclic ring which has one or more hetero atoms in the ring, preferably has 2 to 6 carbon atoms and 1 to 3 heteroatoms, including aziridinyl, azetidinyl, piperidinyl, morpholinyl(including morpholino), pyrrolidinyl, pyrazolidinyl, piperazinyl, tetrahydropyrazolyl, pyrazolinyl, tetrahydropyranyl and etc.

The term "treating", as used herein, refers to reversing, alleviating, inhibiting the progress of, or preventing the disorder or condition to which such term applies, or one or more symptoms of such disorder or condition. The term "treatment" as used herein refers to the act of treating, as "treating" is defined immediately above.

The substitutents "$R^3$" can be bonded at carbon atom which connects "B group" and "$R^3$ group"), such as formula as follows:

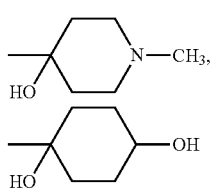
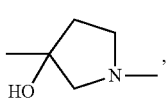

A preferred compound of formula (I) of this invention is that wherein Het represents a heterocyclic group selected from

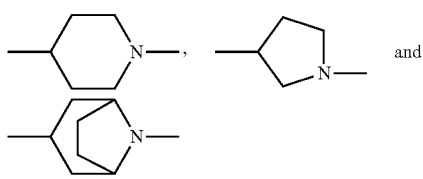

said heterocyclic group being unsubstituted or substituted by 1 to 3 substituents independently selected from the group consisting of substituents $\alpha^1$.

A much preferred compound of formula (I) of this invention is that wherein Het represents a group of formula

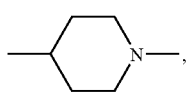

and this group being unsubstituted or substituted by one substituent selected from the group consisting of substituents $\alpha^1$;
A represents an alkylene group having from 1 to 3 carbon atoms; and
$R^1$ represents an isopropyl group or a cyclopentyl group.

A much preferred compound of formula (I) of this invention is that wherein Het represents a group of formula

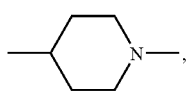

A represents an alkylene group having from 1 to 2 carbon atoms;
B represents an alkylene group having from 1 to 5 carbon atoms;
$R^3$ independently represents
  (i) an oxo group, a hydroxy group, an amino group, an alkylamino group or a carboxyl group;
  (ii) a cycloalkyl group having from 5 to 7 carbon atoms, and said cycloalkyl group being substituted by 1 to 3 substituents independently selected from the group consisting of substituents $\alpha^2$, or
  (iii) a heterocyclic group having from 5 to 7 atoms, and said heterocyclic group being unsubstituted or substituted by 1 to 3 substituents independently selected from the group consisting of substituents $\beta$,
said substituents $\alpha^2$ are independently selected from a hydroxy group, an amino group, a hydroxy-substituted alkyl group having from 1 to 4 carbon atoms, a carboxyl group and an alkoxy group having from 1 to 4 carbon atoms; and
said substituents $\beta$ are selected from a hydroxy group, a hydroxy-substituted alkyl group having from 1 to 4 carbon atoms, a carboxyl group, an amino group, an alkyl group having from 1 to 4 carbon atoms, an amino-substituted alkyl group having from 1 to 4 carbon atoms and a carbamoyl group; and n is 1, 2, or 3.

A much preferred compound of formula (I) of this invention is that wherein
A represents a methylene group;
B represents an alkylene group having from 1 to 5 carbon atoms;

$R^1$ represents an isopropyl group;
$R^3$ independently represents
  (i) an oxo group or a hydroxy group;
  (ii) a cycloalkyl group having from 5 to 6 carbon atoms, and said cycloalkyl group being substituted by 1 to 2 substituents independently selected from the group consisting of substituents $\alpha^2$, or
  (iii) a heterocyclic group having from 5 to 6 atoms, and said heterocyclic group being unsubstituted or substituted by 1 to 2 substituents independently selected from the group consisting of substituents $\beta$,
said substituents $\alpha^2$ are independently selected from a hydroxy group or an amino group; and
said substituents $\beta$ are selected from a hydroxy group, an amino group and an alkyl group having from 1 to 4 carbon atoms group; and n is 1 or 2.

A much preferred compound of formula (I) of this invention is that wherein
B represents an alkylene group having from 1 to 3 carbon atoms;
$R^3$ independently represents
  (i) an oxo group or a hydroxy group;
  (ii) a cyclohexyl group substituted by 1 to 2 hydroxy group, or
  (iii) a heterocyclic group selected from a hydroxytetrahydropyranyl, piperidinyl and morpholinyl, and said heterocyclic group being unsubstituted or substituted by 1 to 2 substituents independently selected from a hydroxy group and a methyl group; and n is 1 or 2.

A much preferred compound of formula (I) of this invention is that wherein
B represents a methylene group;
$R^2$ represents a methyl group;
$R^3$ independently represents a 1, 4 dihytdroxycyclohexyl group, a hydroxytetrahydropyranyl, piperidinyl and morpholinyl; and n is 1.

A much preferred compound of formula (I) of this invention is that wherein
$R^3$ independently represents a 1, 4 dihytdroxycyclohexyl group or a hydroxytetrahydropyranyl.

General Synthesis

The compounds of the present invention may be prepared by a variety of processes well known for the preparation of compounds of this type, for example as shown in the following reaction Schemes. Unless otherwise indicated $R^1$, $R^2$, $R^3$, Het and n in the reaction Schemes and discussion that follow are defined as above. The term "protecting group", as used hereinafter, means a hydroxy or amino protecting group which is selected from typical hydroxy or amino protecting groups described in Protective Groups in Organic Synthesis edited by T. W. Greene et al. (John Wiley & Sons, 1991); All starting materials in the following general syntheses may be commercially available or obtained by conventional methods known to those skilled in the art.

The compound of formula (I) can be prepared by a similar manner or a method known to a skilled person.

Synthesis of Compound of Formula (I):

The following reaction Schemes illustrate the preparation of compounds of formula I.

Scheme 1:

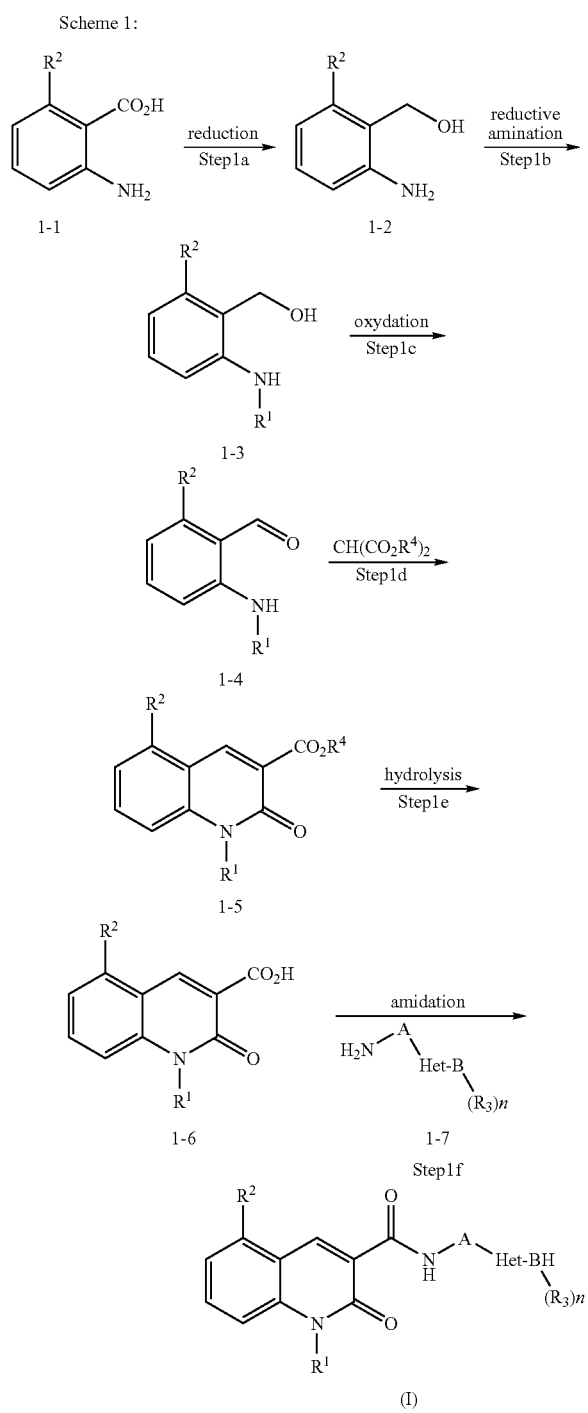

Step 1a

A compound of formula 1-2 can be prepared by reduction of compound of formula 1-1 with a suitable reducing agent such as, sodium borohydride (NaBH$_4$), lithium aluminumhydride (LAH), diborane, borane dimethylsulfide complex, borane-THF, (preferably hydrogen and a metal catalyst), usually in excess, in a reaction inert solvent such as diethyl ether, DME, dioxane, terahydrofuran (THF) (preferably THF), generally at temperature of −78° C. to 60° C., preferably from about 0° C. to 45° C. for 5 minutes to 24 hours, preferably 60 minutes to 12 hours.

Step 1b

In step 1b, a compound of formula 1-3 can be prepared by the reductive amination of the alkanone compound with an amine compound of formula 1-2 in the presence or absence of a reducing agent or a metal agent in an inert solvent.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable aqueous or non-aqueous organic solvents include: alcohols, such as methanol, ethanol or isopropanol; ethers, such as tetrahydrofuran, dimethoxyethane or dioxane; acetonitrile; N,N'-dimethylformamide; dimethylsulfoxide; acetic acid; and halogenated hydrocarbon, such as dichloromethane, dichloroethane or chloroform.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction with reducing agents at a temperature of from −78° C. to 100° C., more preferably from about −20° C. to 60° C. The time required for the reaction may also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice. In the case of the reaction with metal reagents, it is convenient to carry out the reaction at a temperature of from 20° C. to 100° C., preferably from about 20° C. to 60° C. for 10 minutes to 48 hours, preferably 30 minutes to 24 hours.

Suitable reducing reagents are those typically used in the reduction including, for example, sodium borohydride, sodium cyanoborohydride, sodium triacetoxyborohydride.

Example of suitable metal reagents include palladium-carbon, palladiumhydroxide-carbon, platinumoxide, platinum-carbon, ruthenium-carbon, rhodium-aluminumoxide and tris[triphenyphosphine]rhodiumchloride. The reduction with metal reagents may be carried out under hydrogen atmosphere at a pressure ranging from 1 to 100 atm, preferably from 1 to 10 atm.

This reduction can be carried out after formation of the corresponding enamine of the alkanone compound or imine of the alkanone compound in a reaction-inert solvent such as benzene, toluene, or xylene at a temperature in the range from 20 to 130° C. for 1 hour to 1 week.

Step 1c

The compound 1-4 can be reacted with a compound of formula 1-3 in the presence of a oxydating agent such as manganese dioxide, pyridinium chlorochromate, pyridinium dichromate (preferably manganese dioxide), usually in excess, in a reaction inert solvent such as dimethoxyethane, dioxane, acetonitrile, N,N'-dimethylformamide, dimethylsulfoxide, dichloromethane, dichloroethane, terahydrofuran (THF), benzene, toluene, or chloroform (preferably benzene or toluene), generally at temperature of −78° C. to 120° C., preferably from about 0° C. to 90° C. for 5 minutes to 24 hours, preferably 60 minutes to 12 hours.

Step 1d

The compound 1-3 can be reacted with a compound of formula CH(CO$_2$R$^4$)$_2$ wherein R$^4$ is methyl or ethyl, in a reaction inert solvent such as dimethoxyethane, dioxane, acetonitrile, N,N'-dimethylformamide, dimethylsulfoxide, dichloromethane, dichloroethane, terahydrofuran (THF), benzene, toluene, or chloroform (preferably benzene), generally at temperature of −78° C. to 120° C., preferably from about 0° C. to 90° C. for 5 minutes to 24 hours, preferably 60 minutes to 12 hours.

Step 1e

In this Step, an acid compound of formula 1-6 may be prepared by hydrolysis of the ester compound of formula 1-5 in a solvent.

The hydrolysis may be carried out by conventional procedures. In a typical procedure, the hydrolysis carried out under the basic condition, e.g. in the presence of sodium hydroxide, potassium hydroxide or lithium hydroxide. Suitable solvents include, for example, water, alcohols such as methanol, ethanol, propanol, butanol, 2-methoxyethanol, and ethylene glycol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from −20 to 100° C., usually from 20° C. to 65° C. for 30 minutes to 24 hours, usually 60 minutes to 10 hour.

The hydrolysis may also be carried out under the acidic condition, e.g. in the presence of e.g. in the presence of hydrogen halides, such as hydrogen chloride and hydrogen bromide; sulfuric acid; sulfonic acids, such as p-toluenesulfonic acid and benzenesulfonic acid; pyridium p-toluenesulfonate; and carboxylic acid, such as acetic acid and trifluoroacetic acid. Suitable solvents include, for example, water; alcohols such as methanol, ethanol, propanol, butanol, 2-methoxyethanol, and ethylene glycol; ethers such as tetrahydrofuran (THF), 1,2-dimethoxyethane (DME), and 1,4-dioxane; amides such as N,N-dimethylformamide (DMF) and hexamethylphospholictriamide; and sulfoxides such as dimethyl sulfoxide (DMSO). This reaction may be carried out at a temperature in the range from −20 to 100° C., usually from 20° C. to 65° C. for 30 minutes to 24 hours, usually 60 minutes to 10 hour.

Alternatively, the compound of 1-6 can be prepared from a compounds of formula 1-4 by using meldrum's acid condensation in a reaction condition known to a skilled person (Masaji Suzuki et al., *Heterocycles*, 53, 2471 (2000))

Step 1f

In this Step, an amide compound of formula (I) may be prepared by the coupling reaction of an amine compound of formula 1-7 with the acid compound of formula 1-6 in the presence or absence of a coupling reagent in an inert solvent. If desired, this reaction may be carried out in the presence or absence of an additive such as 1-hydroroxybenzotriazole or 1-hydroxyazabenzotriazole.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: acetone, nitromethane, DMF, sulfolane, DMSO, NMP, 2-butanone, acetonitrile; halogenated hydrocarbons, such as dichloromethane, dichloroethane, chloroform; and ethers, such as tetrahydrofuran and dioxane.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 60° C. The time required for the reaction may also vary widely, depending on many factors, notably the reaction temperature and the nature of the reagents and solvent employed. However, provided that the reaction is effected under the preferred conditions outlined above, a period of 5 minutes to 1 week, more preferably 30 minutes to 24 hours, will usually suffice.

Suitable coupling reagents are those typically used in peptide synthesis including, for example, diimides (e.g., dicyclohexylcarbodiimide (DCC), water soluble carbodiimide (WSC)), 2-ethoxy-N-ethoxycarbonyl-1,2-dihydroquinoline, 2-bromo-1-ethylpyridinium tetrafluoroborate (BEP), 2-chloro-1,3-dimethylimidazolinium chloride, benzotriazol-1-yloxy-tris(dimethylamino)phosphonium hexafluorophosphate (BOP), diethyl azodicarboxylate-triphenylphosphine, diethylcyanophosphate, diethylphosphorylazide, 2-chloro-1-methylpyridinium iodide, N,N'-carnbonyldiimidazole, benzotriazole-1-yl diethyl phosphate, ethyl chloroformate or isobutyl chloroformate. If desired, the reaction may be carried out in the presence of a base such as, N,N-diisopropylethylamine, N-methylmorpholine and triethylamine.

A compound of 1-7 can be prepared from a compounds of formula 2-1 or 2-3 in a reaction condition known to a skilled person as indicated by Scheme 2.

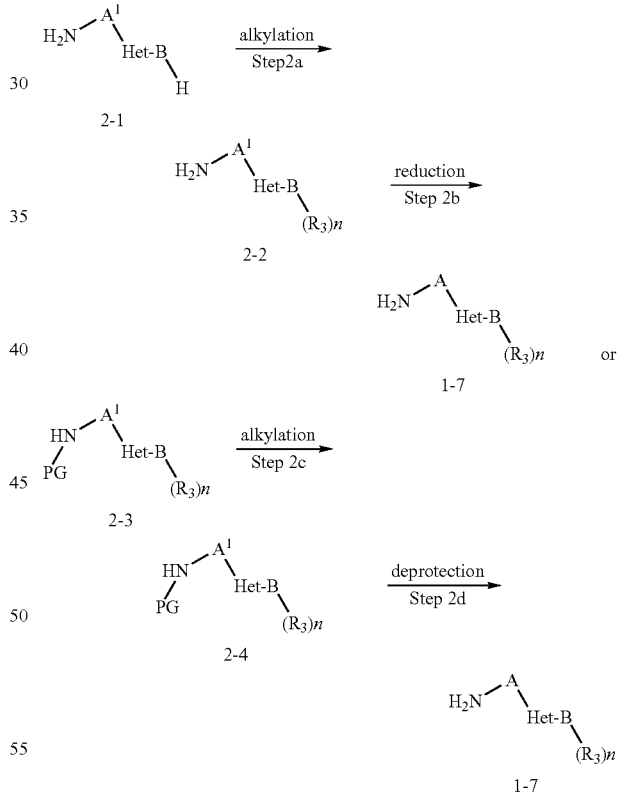

(wherein PG is a protecting group, preferably such as tert-butoxycarbonyl or benzyloxycarbonyl; and $A^1$ is an alkanoyl group having 1 to 4 carbon atoms)

In step 2a, and 2c, a compound of formula 2-2 and 2-4 can be prepared by alkylation of compound of formula 2-1 and 2-3.

The reaction can take place over a wide range of temperatures, and the precise reaction temperature is not critical to the invention. The preferred reaction temperature will depend upon such factors as the nature of the solvent, and the starting material or reagent used. However, in general, it is convenient to carry out the reaction at a temperature of from 0° C. to 120° C., more preferably from 0° C. to 70° C. The time required for the reaction may also vary widely, depending on many factors, notably the reaction temperature and the nature of the reagents and solvent employed. However, provided that the reaction may be effected under the preferred conditions outlined above, a period of from 5 minutes to 48 hours, more preferably from 30 minutes to 24 hours, will usually suffice.

In step 2b, the reduction may be carried out in an essential same condition as one in step 1a.

Alternatively, some of compounds of formula (I) can be prepared by a method indicated by scheme 3 as follows in a condition known to a skilled person.

Scheme 3:

Alternative route to 1-5

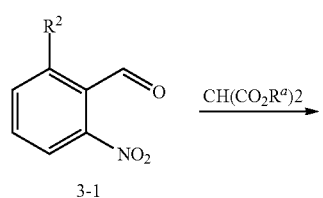

3-1

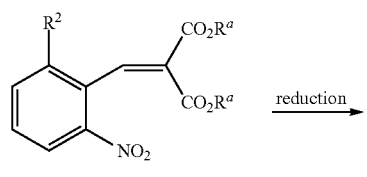

3-2

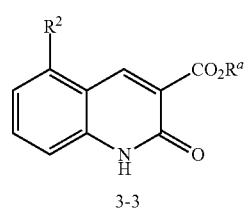

3-3

(wherein $R^a$ methyl or ethyl)

if $R^b$ is protective group such as Boc:

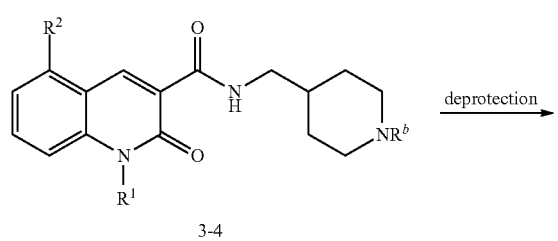

3-4

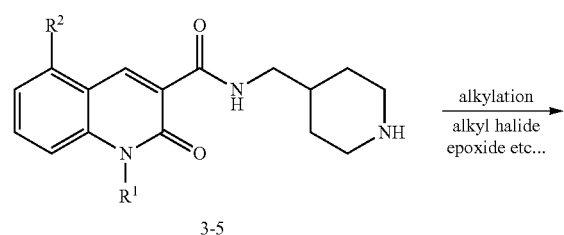

3-5

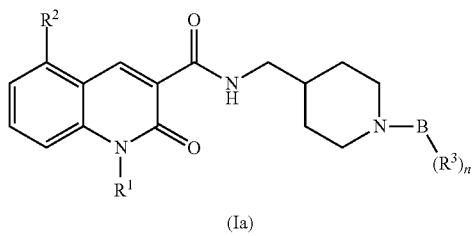

(Ia)

if B-$(R^3)_n$ is piperidine derivative:

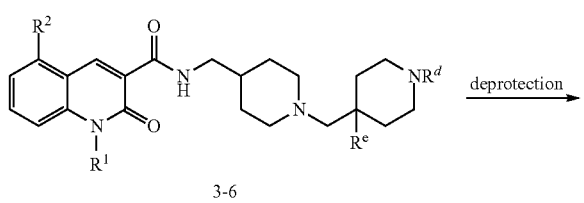

3-6

$R^d$: protective group

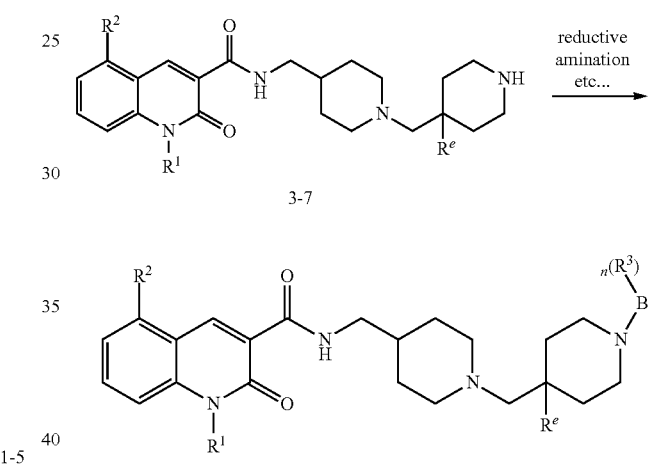

3-7

(Ib)

(wherein $R^e$ is hydroxy)

if B-$(R^3)_n$ is acetic acid derivative:

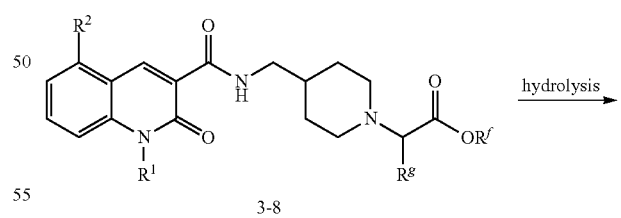

3-8

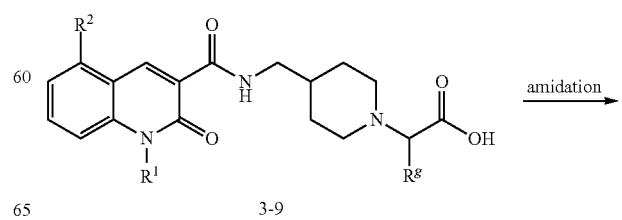

3-9

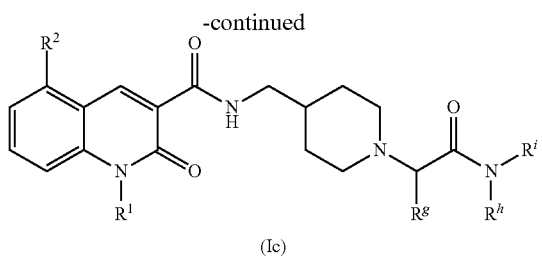

(Ic)

(wherein R$^g$ is such as C1-4 alkyl, R$^f$ is C1-4 alkyl, R$^g$ is C1-4 alkyl, R$^h$ and R$^i$ are C1-4 alkyl or may together form a morpholinyl or piperidinyl.)

The compounds of formula (I), and the intermediates above-mentioned preparation methods can be isolated and purified by conventional procedures, such as distillation, recrystallization or chromatographic purification.

The optically active compounds of this invention can be prepared by several methods. For example, the optically active compounds of this invention may be obtained by chromatographic separation, enzymatic resolution or fractional crystallization from the final compounds.

Several compounds of this invention possess an asymmetric center. Hence, the compounds can exist in separated (+)- and (−)-optically active forms, as well as in racemic one thereof. The present invention includes all such forms within its scope. Individual isomers can be obtained by known methods, such as optically selective reaction or chromatographic separation in the preparation of the final product or its intermediate.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, pharmaceutically acceptable esters of said compounds and pharmaceutically acceptable salts of said compounds, of said esters or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assay. Tritiated, i.e., $^3$H, and carbon-14, i.e., $^{14}$C, isotopes are particularly preferred for their ease of presentation and detectability. Further, substitution with heavier isotopes such as deuterium, i.e., $^2$H, can afford therapeutic advantage resulting from greater metabolic stability, for example increased in vivo half-life or reduced dosage requirement and, hence, may be preferred in some circumstances. Isotopically labeled compounds of formula (I) of this invention and prodrugs thereof can generally be prepared by carrying out the procedure disclosed in above-disclosed Schemes and/or Examples and Preparations below, by submitting a readily available isotopically labeled reagent for a non-isotopically labeled reagent.

The present invention includes salt forms of the compounds (I) as obtained.

Certain compounds of the present invention may be capable of forming pharmaceutically acceptable non-toxic cations. Pharmaceutically acceptable non-toxic cations of compounds of formula (I) may be prepared by conventional techniques by, for example, contacting said compound with a stoichiometric amount of an appropriate alkali or alkaline earth metal (sodium, potassium, calcium and magnesium) hydroxide or alkoxide in water or an appropriate organic solvent such as ethanol, isopropanol, mixtures thereof, or the like.

The bases which are used to prepare the pharmaceutically acceptable base addition salts of the acidic compounds of this invention of formula (I) are those which form non-toxic base addition salts, i.e., salts containing pharmaceutically acceptable cations, such as adenine, arginine, cytosine, lysine, benethamine (i.e., N-benzyl-2-phenyletylamine), benzathine (i.e., N,N-dibenzylethylenediamine), choline, diolamine (i.e., diethanolamine), ethylenediamine, glucosamine, glycine, guanidine, guanine, meglumine (i.e., N-methylglucamine), nicotinamide, olamine (i.e., ethanolamine), ornithine, procaine, proline, pyridoxine, serine, tyrosine, valine and tromethamine (i.e., tris or tris(hydroxymethyl)aminomethane). The base addition salts can be prepared by conventional procedures.

Insofar as the certain compounds of this invention are basic compounds, they are capable of forming a wide variety of different salts with various inorganic and organic acids.

The acids which are used to prepare the pharmaceutically acceptable acid addition salts of the basic compounds of this invention of formula (I) are those which form non-toxic acid addition salts, i.e., salts containing pharmaceutically acceptable anions, such as the chloride, bromide, iodide, nitrate, sulfate or bisulfate, phosphate or acid phosphate, acetate, lactate, citrate or acid citrate, tartrate or bi-tartrate, succinate, malate, fumarate, gluconate, saccharate, benzoate, methanesulfonate, ethanesulfonate, benzenesulfonate, p-toluenesulfonate, adipate, aspartate camsylate, edisylate (i.e., 1,2-ethanedisulfonate), estolate (i.e., laurylsulfate), gluceptate (i.e., gluscoheptonate), gluconate, 3-hydroxy-2-naphthoate, xionofoate (i.e., 1-hydroxy-2-naphthoate), isethionate, (i.e., 2-hydroxyethanesulfonate), mucate (i.e., galactarate), 2-naphsylate (i.e., naphthalenesulphonate, stearate, cholate, glucuronate, glutamate, hippurate, lactobionate, lysinate, maleate, mandelate, napadisylate, nicatinate, polygalacturonate, salicylate, sulphosalicylate, tannate, tryptophanate, borate, carbonate, oleate, phthalate and pamoate (i.e., 1,1'-methylene-bis-(2-hydroxy-3-naphthoate). The acid addition salts can be prepared by conventional procedures.

For a review of on suitable salts see Berge et al., J. Pharm. Sci., 66, 1-19, 1977.

Also included within the scope of this invention are bioprecursors (also called pro-drugs) of the compounds of the formula (I). A bioprecursor of a compound of the formula (I) is a chemical derivative thereof which is readily converted back into the parent compound of the formula (I) in biological systems. In particular, a bioprecursor of a compound of the formula (I) is converted back to the parent compound of the formula (I) after the bioprecursor has been administered to, and absorbed by, a mammalian subject, e.g., a human subject. For example, it is possible to make a bioprecursor of the compounds of formula (I) in which one or both of L and W include hydroxy groups by making an ester of the hydroxy group. When only one of L and W includes hydroxy group, only mono-ester is possible. When both L and W include hydroxy, mono- and di-esters (which can be the same or different) can be made. Typical esters are simple alkanoate esters, such as acetate, propionate, butyrate, etc. In addition, when L or W includes a hydroxy group, bioprecursors can be made by converting the hydroxy group to an acyloxymethyl derivative (e.g., a pivaloyloxymethyl derivative) by reaction with an acyloxymethyl halide (e.g., pivaloyloxymethyl chloride).

When the compounds of the formula (I) of this invention may form solvates such as hydrates, such solvates are included within the scope of this invention.

Method for Assessing Biological Activities:

The 5-HT$_4$ receptor binding affinities of the compounds of this invention are determined by the following procedures.

Membrane Preparation

Pig heads were supplied from an abattoir. Striatal tissues were dissected, weighed and homogenized in 15 volumes of 50 mM ice-cold HEPES (pH 7.5) in a Polytron homogenizer (30 sec at full speed). Suspension was centrifuged at 48,000 g and 4° C. for 15 min. The resulting pellet was resuspended in an appropriate volume of 50 mM ice-cold HEPES, dispensed into aliquots and stored at −80° C. until use.

Bovine heads were also supplied from an abattoir. Striatal tissues were dissected, weighed and homogenized in 20 volumes of 50 mM ice-cold Tris-HCl (pH 7.4) in a Polytron homogenizer (30 sec at full speed). Suspension was centrifuged at 20,000 g and 4° C. for 30 min. The resulting pellet was resuspended in 15 volumes of 50 mM ice-cold Tris-HCl, homogenized and centrifuged again in the same way. The final pellet was resuspended in an appropriate volume of 50 mM Tris-HCl, dispensed into aliquots and stored at −80° C. until use.

Cerebral cortical tissues were removed from male Sprague-Dawley (SD) rats (Japan SLC), weighed and placed in 10 volumes of 50 mM ice-cold Tris-HCl (pH 7.5). This was homogenized in a Polytron homogenizer (30 sec at full speed) and subsequently centrifuged at 48,000 g and 4° C. for 15 min. The resulting pellet was resuspended in 50 mM ice-cold Tris-HCl, homegenized and centrifuged again in the same way. The final pellet was resuspended in an appropriate volume of 50 mM Tris-HCl, dispensed into aliquots and stored at −80° C. until use.

The protein concentrations of homogenates were determined by Bradford method or BCA protein method (Pierce) with BSA as a standard.

Binding Assays

Affinity of compounds for pig or bovine 5-HT$_4$ and rat 5-HT$_3$ receptors were assessed with using radiolabeled specific ligands, GR 113808 ({1-[2-(methylsulfonyl)ethyl]-4-piperidinyl}[methyl-3H]-1H-indole-3-carboxylate) and BRL 43694 (1-Methyl-N-(9-[methyl-3H]-9-azabicyclo[3.3.1]non-3-yl)-1H-indazole-3-caboxamide). Compounds were incubated with 25-100 pM of [$^3$H]-GR 113808 (Amersham) and 0.6-1 mg protein of pig or bovine striatal membranes suspended in a final volume of 0.8-1 ml of 50 mM Tris-HCl (pH 7.5). Nonspecific binding was determined with 10-50 µM 5-HT. The binding of 0.3 nM [$^3$H]-BRL 43694 (NEN) was measured using 400 µg protein of rat cortical membranes suspended in a final volume of 500 µl of 50 mM Tris-HCl (pH 7.5). Nonspecific binding was determined with 10 µM 5-HT.

The plates were incubated at room temperature on a plate shaker for 30 min. The assays were stopped by rapid filtration using a Brandell cell harvester through Wallac-B filters presoaked in 0.2% poly(ethylenimine) at 4° C. for 60-90 min. The filters were washed three times with 1 ml of ice-cold 50 mM HEPES, and were dried in a microwave or at room temperature. They were bagged and heated with meltilex scintillant (Wallac) or soaked in BetaplateScint (Wallac). Receptor-bound radioactivity was quantified using Big-spot counter, Betaplate counter (Wallac) or LS counter (Packard).

Human 5-HT$_4$ Binding

Human 5-HT$_{4(d)}$ transfected HEK293 cells were prepared and grown in-house. The collected cells were suspended in 50 mM HEPES (pH 7.4 at 4° C.) supplemented with protease inhibitor cocktail (Boehringer, 1:1000 dilution) and homogenized using a hand held Polytron PT 1200 disruptor set at full power for 30 sec on ice. The homogenates were centrifuged at 40,000×g at 4° C. for 30 min. The pellets were then resuspended in 50 mM HEPES (pH 7.4 at 4° C.) and centrifuged once more in the same manner. The final pellets were resuspended in an appropriate volume of 50 mM HEPES (pH 7.4 at 25° C.), homogenized, aliquoted and stored at −80° C. until use. An aliquot of membrane fractions was used for protein concentration determination using BCA protein assay kit (PIERCE) and ARVOsx plate reader (Wallac).

For the binding experiments, 25 µl of test compounds were incubated with 25 µl, of [$^3$H]-GR113808 (Amersham, final 0.2 nM) and 150 µl of membrane homogenate and WGA-SPA beads (Amersham) suspension solutions (10 µg protein and 1 mg SPA beads/well) for 60 minutes at room temperature. Nonspecific binding was determined by 1 µM GR113808 (Tocris) at the final concentration. Incubation was terminated by centrifugation at 1000 rpm. Receptor-bound radioactivity was quantified by counting with MicroBeta plate counter (Wallac).

All compounds prepared in the working examples as described below were tested by this method, and they showed Ki values from 1.5 nM to 8.6 nM with respect to inhibition of binding at the 5-HT$_4$ receptor.

Functional Assay:

The presence of 5-HT$_4$ receptors in the rat oesophagus and the ability to demonstrate partial agonism in the TMM preparation are reported in the literature (See G. S. Baxter et al. Naunyn-Schmiedeberg's Arch Pharmacol (1991) 343: 439-446; M. Yukiko et al. JPET (1997) 283:1000-1008; and J. J. Reeves et al. Br. J. Pharmacol. (1991) 103: 1067-1072). More specifically, partial agonist activity can be measured according to the following procedures.

Male SD rats (Charles River) weighing 250-350 g were stunned and then killed by cervical dislocation. The oesophagus was dissected from immediately proximal to the stomach (including piece of stomach to mark distal end) up to the level of the trachea and then placed in fresh Krebs' solution.

The outer skeletal muscle layer was removed in one go by peeling it away from the underlying smooth muscle layer using forceps (stomach to tracheal direction). The remaining inner tube of smooth muscle was known as the TMM. This was trimmed to 2 cm from the original 'stomach-end' and the rest discarded.

The TMMs were mounted as whole 'open' tubes in longitudinal orientation in 5 ml organ baths filled with warm (32° C.) aerated Krebs. Tissues were placed under an initial tension of 750 mg and allowed to equilibrate for 60 minutes. The tissues were re-tensioned twice at 15 minute intervals during the equilibration period. The pump flow rate was set to 2 ml/min during this time.

Following equilibration, the pump was switched off. The tissues were exposed to 1 µM carbachol and contracted and reached a steady contractile plateau within 15 minutes. Tissues were then subject to 1 µM 5-HT (this was to prime the tissues). The tissues relaxed in response to 5-HT fairly rapidly—within 1 minute. As soon as maximal relaxation has occurred and a measurement taken, the tissues were washed at maximum rate (66 ml/min) for at least 1 minute and until the original baseline (pre-carbachol and 5-HT) has returned (usually, the baseline drops below the original one following initial equilibration). The pump flow rate was reduced to 2 ml/min and the tissues left for 60 minutes.

A cumulative concentration-effect-curve (CEC) to 5-HT was constructed across the range 0.1 nM to 1 μM, in half-log unit increments (5-HT curve 1 for data analysis). Contact time between doses was 3 minutes or until plateau established. Tissues responded quicker as concentration of 5-HT in the bath increases. At the end of the curve, the tissues were washed (at maximum rate) as soon as possible to avoid desensitisation of receptors. Pump rate was reduced to 2 ml/min and the tissues left for 60 minutes.

A second CEC was carried out—either to 5-HT (for time control tissues), another 5-HT$_4$ agonist (standard) or a test compound (curve 2 for data analysis). Contact time varied for other 5-HT$_4$ agonists and test compounds and was tailored according to the tissues' individual responses to each particular agent. In tissues exposed to a test compound, a high concentration (1 μM) of a 5-HT$_4$ antagonist (SB 203,186: 1H-Indole-3-carboxylic acid, 2-(1-piperidinyl)ethyl ester, Tocris) was added to the bath following the last concentration of test compound. This was to see if any agonist-induced relaxation (if present) could be reversed. SB 203,186 reversed 5-HT induced relaxation, restoring the tissue's original degree of carbachol-induced tone.

Agonist activity of test compounds was confirmed by pre-incubating tissues with 100 nM standard 5HT$_4$ antagonist such as SB 203,186. SB 203,186 was added to the bath 5 minutes before the addition of carbachol prior to curve 2. Tissues must be 'paired' for data analysis i.e. the test compound in the absence of SB 203,186 in one tissue was compared with the test compound in the presence of SB 203,186 in a separate tissue. It was not possible to carry out a curve 3 i.e. 5-HT curve 1, followed by the test compound curve 2 (−SB 203,186), followed by the test compound curve 3 (+SB 203,186).

Agonist-Induced cAMP Elevation in Human 5-HT$_{4(d)}$ Transfected HEK293 Cells

Human 5-HT$_{4(d)}$ transfected HEK293 cells were established in-house. The cells were grown at 37° C. and 5% CO$_2$ in DMEM supplemented with 10% FCS, 20 mM HEPES (pH 7.4), 200 μg/ml hygromycin B (Gibco), 100 units/ml penicillin and 100 μg/ml streptomycin.

The cells were grown to 60-80% confluence. On the previous day before treatment with compounds dialyzed FCS (Gibco) was substituted for normal and the cells were incubated overnight.

Compounds were prepared in 96-well plates (12.5 μl/well). The cells were harvested with PBS/1 mM EDTA, centrifuged and washed with PBS. At the beginning of the assay, cell pellet was resuspended in DMEM supplemented with 20 mM HEPES, 10 μM pargyline (Sigma) and 1 mM 3-isobutyl-1-methylxanthine (Sigma) at the concentration of 1.6×10$^5$ cells/ml and left for 15 minutes at room temperature. The reaction was initiated by addition of the cells into plates (12.5 μl/well). After incubation for 15 minutes at room temperature, 1% Triton X-100 was added to stop the reaction (25 μL/well) and the plates were left for 30 minutes at room temperature. Homogenous time-resolved fluorescence-based cAMP (Schering) detection was made according to the manufacturer's instruction. ARVOsx multilabel counter (Wallac) was used to measure HTRF (excitation 320 nm, emission 665 nm/620 nm, delay time 50 μs, window time 400 μs).

Data was analyzed based on the ratio of fluorescence intensity of each well at 620 nm and 665 nm followed by cAMP quantification using cAMP standard curve. Enhancement of cAMP production elicited by each compound was normalized to the amount of cAMP produced by 1000 nM serotonin (Sigma).

All compounds of Examples showed 5HT$_4$ receptor agonistic activity.

Human Dofetilide Binding

Human HERG transfected HEK293S cells were prepared and grown in-house. The collected cells were suspended in 50 mM Tris-HCl (pH 7.4 at 4° C.) and homogenized using a hand held Polytron PT 1200 disrupter set at full power for 20 sec on ice. The homogenates were centrifuged at 48,000×g at 4° C. for 20 min. The pellets were then resuspended, homogenized, and centrifuged once more in the same manner. The final pellets were resuspended in an appropriate volume of 50 mM Tris-HCl, 10 mM KCl, 1 mM MgCl$_2$ (pH 7.4 at 4° C.), homogenized, aliquoted and stored at −80° C. until use. An aliquot of membrane fractions was used for protein concentration determination using BCA protein assay kit (PIERCE) and ARVOsx plate reader (Wallac).

Binding assays were conducted in a total volume of 200 μl in 96-well plates. Twenty μl of test compounds were incubated with 20 μl of [$^3$H]-dofetilide (Amersham, final 5 nM) and 160 μl of membrane homogenate (25 μg protein) for 60 minutes at room temperature. Nonspecific binding was determined by 10 μM dofetilide at the final concentration. Incubation was terminated by rapid vacuum filtration over 0.5% presoaked GF/B Betaplate filter using Skatron cell harvester with 50 mM Tris-HCl, 10 mM KCl, 1 mM MgCl$_2$, pH 7.4 at 4° C. The filters were dried, put into sample bags and filled with Betaplate Scint. Radioactivity bound to filter was counted with Wallac Betaplate counter.

I$_{HERG}$ Assay

HEK 293 cells which stably express the HERG potassium channel were used for electrophysiological study. The methodology for stable transfection of this channel in HEK cells can be found elsewhere (Z. Zhou et al., 1998, Biophysical journal, 74, pp 230-241). Before the day of experimentation, the cells were harvested from culture flasks and plated onto glass coverslips in a standard MEM medium with 10% FCS. The plated cells were stored in an incubator at 37° C. maintained in an atmosphere of 95% O$_2$/5% CO$_2$. Cells were studied between 15-28 hrs after harvest.

HERG currents were studied using standard patch clamp techniques in the whole-cell mode. During the experiment the cells were superfused with a standard external solution of the following composition (mM); NaCl, 130; KCl, 4; CaCl$_2$, 2; MgCl$_2$, 1; Glucose, 10; HEPES, 5; pH 7.4 with NaOH. Whole-cell recordings was made using a patch clamp amplifier and patch pipettes which have a resistance of 1-3 MOhm when filled with the standard internal solution of the following composition (mM); KCl, 130; MgATP, 5; MgCl$_2$, 1.0; HEPES, 10; EGTA 5, pH 7.2 with KOH. Only those cells with access resistances below 15MΩ and seal resistances >1GΩ was accepted for further experimentation. Series resistance compensation was applied up to a maximum of 80%. No leak subtraction was done. However, acceptable access resistance depended on the size of the recorded currents and the level of series resistance compensation that can safely be used. Following the achievement of whole cell configuration and sufficient for cell dialysis with pipette solution (>5 min), a standard voltage protocol was applied to the cell to evoke membrane currents. The voltage protocol is as follows. The membrane was depolarized from a holding potential of −80 mV to +20 mV for 1000 ms. This was followed by a descending voltage ramp (rate 0.5 mV msec$^{-1}$) back to the holding potential. The voltage protocol was applied to a cell continuously throughout the experiment every 4 seconds (0.25 Hz).

The amplitude of the peak current elicited around −40 mV during the ramp was measured. Once stable evoked current responses were obtained in the external solution, vehicle (0.5% DMSO in the standard external solution) was applied for 10-20 min by a peristalic pump. Provided there were minimal changes in the amplitude of the evoked current response in the vehicle control condition, the test compound of either 0.3, 1, 3, 10 μM was applied for a 10 min period. The 10 min period included the time which supplying solution was passing through the tube from solution reservoir to the recording chamber via the pump. Exposing time of cells to the compound solution was more than 5 min after the drug concentration in the chamber well reached the attempting concentration. There reversibility. Finally, the cells was exposed to high dose of dofetilide (5 μM), a specific IKr blocker, to evaluate the insensitive endogenous current.

All experiments were performed at room temperature (23±1° C.). Evoked membrane currents were recorded on-line on a computer, filtered at 500-1 KHz (Bessel −3 dB) and sampled at 1-2 KHz using the patch clamp amplifier and a specific data analyzing software. Peak current amplitude, which occurred at around −40 mV, was measured off line on the computer.

The arithmetic mean of the ten values of amplitude was calculated under control conditions and in the presence of drug. Percent decrease of $I_N$ in each experiment was obtained by the normalized current value using the following formula: $I_N=(1-I_D/I_C)\times100$, where $I_D$ is the mean current value in the presence of drug and $I_C$ is the mean current value under control conditions. Separate experiments were performed for each drug concentration or time-matched control, and arithmetic mean in each experiment is defined as the result of the study.

Method of Gastric Emptying Model in Rats:

The effects of compounds on gastric emptying in rats were examined by the modified method of D. A. Droppleman et al. (J. Pharmacol. Methods 4, 227-230 (1980)). The test meal, non-fat caloric meal, was prepared according to the method of S. Ueki et al Arzneim.-Forsch./Drug Res. 49 (II), 618-625 (1999)). IGS-SD rats (Male, 7w, 230-270 g) were purchased from Charles River Japan (Atsugi). These rats were used in the experiments after one week acclimatization. In the experiments, rats were fasted 15 hrs before the experiments but allowed free access to water. Forty-five minutes prior to the start of the experiment, water was removed from the cage to prevent rats from taking water. Five minutes before the test meal administration, test compounds, cisapride or vehicle were dosed via an appropriate route to rats (n=8-10) in a volume of 0.1 ml per 100 g body weight. Cisapride (3 mg/kg) was used as a positive control for the experiment. Rats were given 3 ml of the test meal by gavage and were returned to the cages. Thirty minutes after the meal administration, rats were culled by $CO_2$ exposure. Following a midline laparotomy, the stomach is ligated at the lower esophageal sphincter (LES) and pylorus. Then the stomach was removed and weighed (A). After the stomach was opened and rinsed with 0.9% saline, it was blotted the face with the tissue to remove any excess liquid and weighed again (B). After avoiding the rats that had eaten feces or given artificial miss, gastric emptying rate for individual animals was calculated by the formula:

GE rate(%)=(A−B)/weight of the test meal.

Gastric Motility in Conscious Dogs:

The surgical operation in dogs was performed by the modified method of Z. Itoh et al. (Gastroenterol. Jpn., 12, 275-283 (1977)). The effects of test compounds on gastric motility in dogs were examined by the modified method of N. Toshida et al. (J. Pharmacol. Exp/Ther., 257, 781-787 (1991)).

An evaluation in the fasted state: Animals were chronically implanted with a strain gauge force transducer on the gastric body, and fasted overnight prior to the experiment. The gastric motility was continuously recorded by a telemetry system for 8 h after administration of the compound. To quantitate the change in gastrointestinal motility, the motor index was determined as the area under the contraction curves during each 2 h period divided by the peak height of interdigestive migrating contraction.

An evaluation in the postprandial state: Animals were chronically implanted with a strain gauge force transducer on the gastric body, and fasted overnight prior to the experiment. Postprandial motility was induced by feeding with solid meal (100 grams), and the compound was administered 2 h later. The gastric motility was continuously recorded by a telemetry system for 8 h after administration of the compound. The motor index was determined to quantitate the change in gastrointestinal motility as the area under the contraction curves during each 1 h period divided by the area under the contraction curves for 1 h before the compound administration.

The compounds of formula (I) of this invention can be administered via either the oral, parenteral or topical routes to mammals. In general, these compounds are most desirably administered to humans in doses ranging from 0.3 mg to 750 mg per day, preferably from 10 mg to 500 mg per day, although variations will necessarily occur depending upon the weight and condition of the subject being treated, the disease state being treated and the particular route of administration chosen. However, for example, a dosage level that is in the range of from 0.06 mg to 2 mg per kg of body weight per day is most desirably employed for treatment of inflammation.

The compounds of the present invention may be administered alone or in combination with pharmaceutically acceptable carriers or diluents by either of the above routes previously indicated, and such administration can be carried out in single or multiple doses. More particularly, the novel therapeutic agents of the invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging 5% to 70% by weight, preferably 10% to 50% by weight.

For oral administration, tablets containing various excipients such as microcrystalline cellulose, sodium citrate, calcium carbonate, dipotassium phosphate and glycine may be employed along with various disintegrants such as starch and preferably corn, potato or tapioca starch, alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH>8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art. Additionally, it is also possible to administer the compounds of the present invention topically when treating inflammatory conditions of the skin and this may preferably be done by way of creams, jellies, gels, pastes, ointments and the like, in accordance with standard pharmaceutical practice.

EXAMPLES

The invention is illustrated in the following non-limiting examples in which, unless stated otherwise: all operations were carried out at room or ambient temperature, that is, in the range of 18-25° C.; evaporation of solvent was carried out using a rotary evaporator under reduced pressure with a bath temperature of up to 60° C.; reactions were monitored by thin layer chromatography (tlc) and reaction times are given for illustration only; melting points (m.p.) given are uncorrected (polymorphism may result in different melting points); the structure and purity of all isolated compounds were assured by at least one of the following techniques: tlc (Merck silica gel 60 $F_{254}$ precoated TLC plates or Merck $NH_2$ $F_{254}$, precoated HPTLC plates), mass spectrometry, nuclear magnetic resonance (NMR), infrared red absorption spectra (IR) or microanalysis. Yields are given for illustrative purposes only. Flash column chromatography was carried out using Merck silica gel 60 (230-400 mesh ASTM) or Fuji Silysia Chromatorex® DU3050 (Amino Type, 30~50 µm). Low-resolution mass spectral data (EI) were obtained on a Integrity (Waters) mass spectrometer or a Automass 120 (JEOL) mass spectrometer. Low-resolution mass spectral data (ESI) were obtained on a ZMD2 (Waters) mass spectrometer or a Quattro II (Micromass) mass spectrometer. NMR data was determined at 270 MHz (JEOL JNM-LA 270 spectrometer) or 300 MHz (JEOL JNM-LA300) using deuterated chloroform (99.8% D) or dimethylsulfoxide (99.9% D) as solvent unless indicated otherwise, relative to tetramethylsilane (TMS) as internal standard in parts per million (ppm); conventional abbreviations used are: s=singlet, d=doublet, t=triplet, q=quartet, m=multiplet, br.=broad, etc. IR spectra were measured by a Shimazu infrared spectrometer (IR-470). Optical rotations were measured using a JASCO DIP-370 Digital Polarimeter (Japan Spectroscopic CO, Ltd.). Chemical symbols have their usual meanings; b.p. (boiling point), m.p. (melting point), l (liter(s)), ml (milliliter(s)), g (gram(s)), mg (milligram(s)), mol (moles), mmol (millimoles), eq. (equivalent(s)).

Example 1

5-CHLORO-N-({1-[(4-HYDROXYTETRAHY-DRO-2H-PYRAN4-YL)METHYL]PIPERIDIN-4-YL}METHYL)-1-ISOPROPYL-2-OXO-1,2-DIHY-DROQUINOLINE-3-CARBOXAMIDE

Step 1. Benzyl({1-[(4-hydroxytetrahydro-2H-pyran-4-yl)methyl]piperidin-4-yl}methyl)carbamate

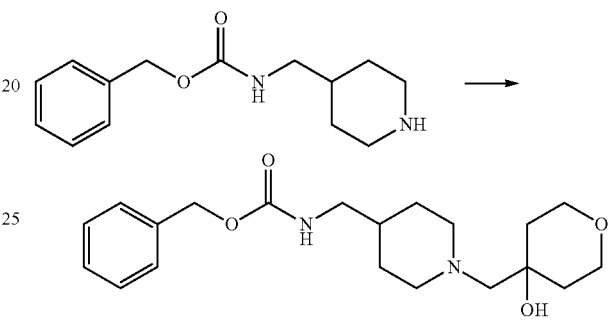

A mixture of benzyl(piperidin-4-ylmethyl)carbamate (7.77 g, 31.3 mmol, Bose, D. Subhas et al., *Tetrahedron Lett.*, 1990, 31, 6903) and 1,6-dioxaspiro[2.5]octane (4.29 g, 37.6 mmol, Satyamurthy, Nagichettiar et al., *Phosphorus Sulfur*, 1984, 19, 113) in methanol (93 mL) was stirred at room temperature for 20 h. Then the mixture was refluxed for 8 h. After cooling to room temperature, the solvent was removed in vacuo. The residue was chromatographed on a column of silica gel eluting with methanol/dichloromethane (1:20) to give 5.60 g (49%) of the title compound as a colorless oil.

$^1$H-NMR (CDCl$_3$) δ: 7.40-7.30 (5H, m), 5.09 (2H, s), 4.85 (1H, br), 3.85-3.72 (4H, m), 3.08 (2H, t, J=6.4 Hz), 2.88-2.83 (2H, m), 2.61 (1H, s), 2.36-2.30 (4H, m), 1.77-1.19 (9H, m).

Step 2. 4-{[4-(Aminomethyl)piperidin-1-yl]methyl}tetrahydro-2H-pyran-4-ol

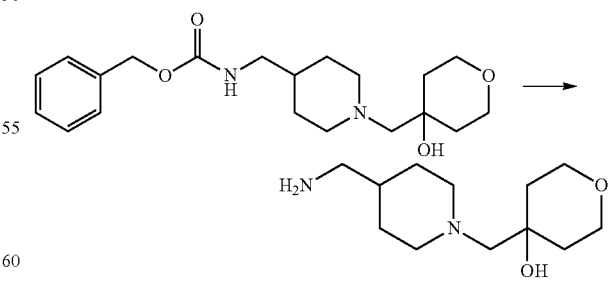

A mixture of benzyl({1-[(4-hydroxytetrahydro-2H-pyran-4-yl)methyl]piperidin-4-yl}methyl)carbamate (5.60 g, 15.5 mmol, step 1) and palladium on activated carbon (10 wt. %, 1.20 g) in methanol (250 mL) was hydrogenated at room temperature for 20 h. Then, the mixture was filtered through a pad of Celite, and the filtrate was concentrated in vacuo to give 3.30 g (94%) of the title compound as slightly yellow oil.

MS (ESI) m/z: 229 (M+H$^+$).

$^1$H-NMR (CDCl$_3$) δ: 1.19-1.28 (2H, m), 1.44-1.63 (8H, m), 1.65-1.71 (2H, m), 2.32 (2H, s), 2.35 (2H, t, J=11.0 Hz), 2.57 (2H, d, J=5.7 Hz), 2.85-2.90 (2H, m), 3.70-3.81 (4H, m).

Step 3. 5-Chloro-N-({1-[(4-hydroxytetrahydro-2H-pyran-4-yl)methyl]piperidin-4-yl}methyl)-1-isopropyl-2-oxo-1,2-dihydroquinoline-3-carboxamide

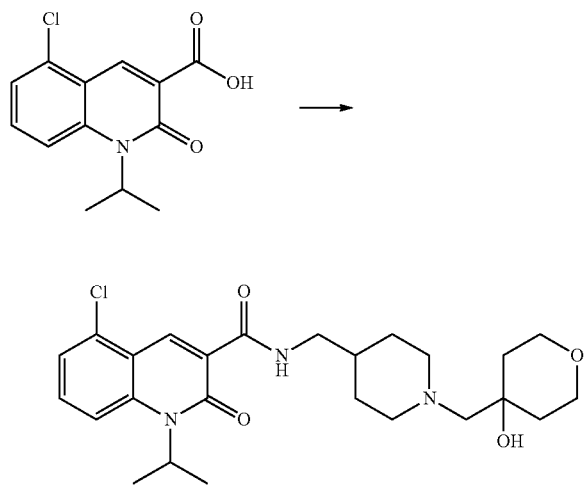

To a solution of 5-chloro-1-isopropyl-2-oxo-1,2-dihydroquinoline-3-carboxylic acid (111 mg, 0.418 mmol, step 4 in preparation 1) in dichloromethane (1 mL) was added oxalyl chloride (0.11 mL, 1.26 mmol) and a drop of N,N-dimethylformamide at 0° C. The mixture was stirred at room temperature for 0.5 h. The solvent and excess amount of oxalyl chloride was removed in vacuo. The residue was dissolved in dichloromethane (1 mL), 4-{[4-(aminomethyl)piperidin-1-yl]methyl}tetrahydro-2H-pyran-4-ol (191 mg, 0.837 mmol, step 2) was added at 0° C. and the mixture was stirred at room temperature for 1 h. Then, the mixture was quenched with water (10 mL), and the aqueous layer was extracted with dichloromethane (20 mL×2). The organic layer was dried over sodium sulfate and concentrated in vacuo. The residue was crystallized from isopropanol to give 156 mg (78%) of the title compound as a white solid.

MS (ESI) m/z: 476 (M+H$^+$).

m.p.: 227° C.

IR (KBr) ν: 3420, 3271, 2945, 2925, 2860, 2788, 2745, 1672, 1609, 1582, 1545, 1447, 1385, 1344, 1205, 1151, 1101, 1015, 984, 985, 845, 802 cm$^{-1}$.

$^1$H-NMR (CDCl$_3$) δ: 9.88 (1H, br m), 9.34 (1H, s), 7.53 (2H, m), 7.35 (1H, m), 3.76 (4H, m), 3.37 (2H, t, J=6.2 Hz), 2.88 (2H, d, J=11.6 Hz), 2.36 (2H, m), 2.31 (2H, s), 1.75 (2H, d, J=12.7 Hz), 1.67 (6H, d, J=7.2 Hz), 1.65-1.30 (7H, m). Signals due to C$\underline{H}$(CH$_3$)$_2$ and O$\underline{H}$ were not observed.

Anal. Calcd. for C$_{25}$H$_{34}$N$_3$O$_4$Cl·0.6H$_2$O: C, 61.68; H, 7.29; N, 8.63. Found: C, 61.38; H, 7.03; N, 8.59.

Alternative route to 4-{[4-(aminomethyl)piperidin-1-yl]methyl}tetrahydro-2H-pyran-4-ol Step 1. tert-butyl({1-[(4-hydroxytetrahydro-2H-pyran-4-yl)methyl]piperidin-4-yl}methyl)carbamate

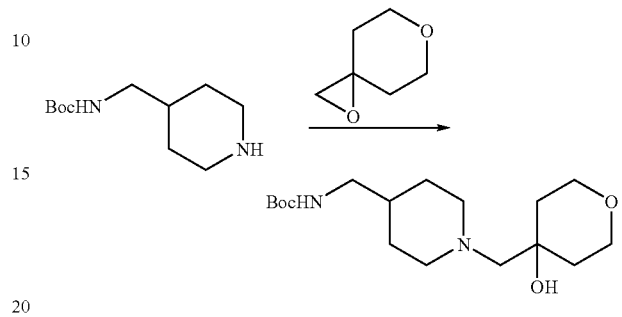

To a stirred solution of tert-butyl(piperidin-4-ylmethyl)carbamate (22.3 g, 104 mmol) in methanol was added 1,6-dioxaspiro[2.5]octane (14.2 g, 124 mmol, Satyamurthy, Nagichettiar et al., *Phosphorus Sulfur*, 1984, 19, 113) at room temperature. Then, the mixture was heated at 60° C. for 4 h. The volatile components were removed by evaporation and the resulting viscous oil was precipitated with a mixture of hexane and diethylether. The precipitate was collected by filtration and recrystallized from a mixture of n-hexane and 2-propanol to give the title compound 14.2 g (42%) as a colorless powder.

MS (ESI) m/z: 329 (M+H$^+$).

m.p.: 104° C.

$^1$H-NMR (CDCl$_3$) δ: 1.23-1.31 (2H, m), 1.44 (9H, s), 1.51-1.69 (8H, m), 2.27-2.38 (4H, m), 2.83-2.88 (2H, m), 3.00 (2H, t, J=6.2 Hz), 3.70-3.85 (4H, m).

Anal. Calcd. for C$_{17}$H$_{32}$N$_2$O$_4$: C, 62.17; H, 9.82; N, 8.53. Found: C, 62.07; H, 9.92; N, 8.58.

Step 2. 4-{[4-(aminomethyl)piperidin-1-yl]methyl}tetrahydro-2H-pyran-4-ol

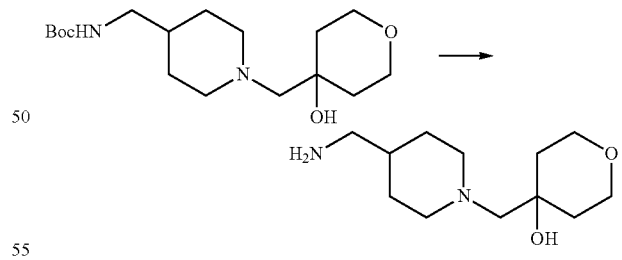

To a solution of tert-butyl({1-[(4-hydroxytetrahydro-2H-pyran-4-yl)methyl]piperidin-4-yl}methyl)carbamate (50.28 g, 153 mmol, step 1) in methanol was added 4N hydrogen chloride in dioxane (200 mL, 800 mmol) at room temperature. After 4 h, the volatile materials were removed by evaporation. The resulting amorphous was precipitated with diethyl ether/methanol (5:1). The precipitate was collected and added to the ice cooled 6N aqueous sodium hydroxide (200 mL) gradually. The mixture was extracted with dichloromethane/methanol (10:1, 500 mL×4). The combined organic phase was washed with brine, dried over magnesium sulfate and concentrated in vacuo to give 24.90 g (99%) of the title compound as a pale brown amorphous.

MS (ESI) m/z: 229 (M+H$^+$).

$^1$H-NMR (CDCl$_3$) δ: 1.19-1.28 (2H, m), 1.44-1.63 (8H, m), 1.65-1.71 (2H, m), 2.32 (2H, s), 2.35 (2H, t, J=11.0 Hz), 2.57 (2H, d, J=5.7 Hz), 2.85-2.90 (2H, m), 3.70-3.81 (4H, m).

Example 2

5-CHLORO-N-({1-[(4-HYDROXYTETRAHY-DRO-2H-PYRAN-4-YL)METHYL]PIPERIDIN-4-YL}METHYL)-1-ISOPROPYL-2-OXO-1,2-DIHY-DROQUINOLINE-3-CARBOXAMIDE ETHANEDIOATE

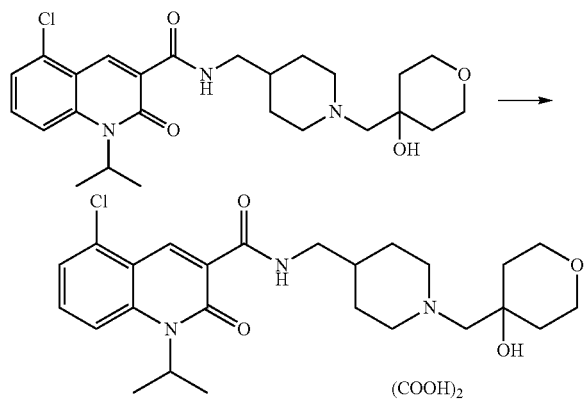

A mixture of 5-chloro-N-({1-[(4-hydroxytetrahydro-2H-pyran-4-yl)methyl]piperidin-4-yl}methyl)-1-isopropyl-2-oxo-1,2-dihydroquinoline-3-carboxamide (27 mg, 0.057 mmol, example 1) and oxalic acid (5.2 mg, 0.057 mmol) was dissolved in methanol and stirred for 1 h. The mixture was concentrated and crystallized from diisopropyl ether to give 6.5 mg (20%) of the title compound as a white solid.

MS (ESI) m/z: 476 (M+H$^+$).

$^1$H-NMR (DMSO-d$_6$) δ: 9.72 (1H, m), 9.01 (1H, s), 7.90 (1H, d, J=8.8 Hz), 7.70 (1H, dd, J=7.9, 8.8 Hz), 7.54 (1H, d, J=7.7 Hz), 3.70-3.15 (14H, br m), 1.75 (2H, br m), 1.57 (6H, d, J=7.0 Hz), 1.64-1.45 (5H, m).

Example 3

N-({1-[(4-HYDROXYTETRAHYDRO-2H-PY-RAN-4-YL)METHYL]PIPERIDIN-4-YL}METHYL)-1-ISOPROPYL-5-METHYL-2-OXO-1,2-DIHYDROQUINOLINE-3-CARBOXAMIDE

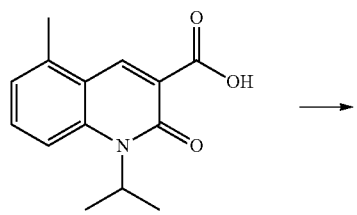

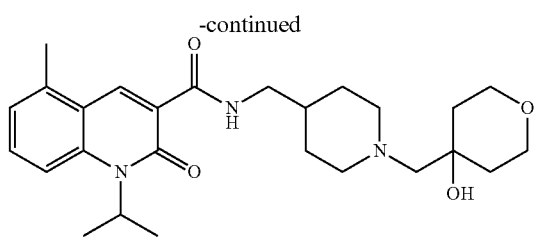

The title compound was prepared according to the procedure of step 3 in the example 1 using 1-isopropyl-5-methyl-2-oxo-1,2-dihydroquinoline-3-carboxylic acid (step 4 in the preparation 2) instead of 5-chloro-1-isopropyl-2-oxo-1,2-dihydroquinoline-3-carboxylic acid.

MS (ESI) m/z: 456 (M+H$^+$).

m.p.: 222° C.

IR (KBr) ν: 3414, 3271, 2926, 2856, 2785, 2742, 1668, 1605, 1587, 1541, 1448, 1380, 1302, 1221, 1153, 1101, 1015, 974, 957, 843, 800, 791 cm$^{-1}$.

$^1$H-NMR (CDCl$_3$) δ: 10.04 (1H, br m), 9.13 (1H, s), 7.50 (2H, m), 7.12 (1H, dd, J=4.0, 4.0 Hz), 3.76 (4H, m), 3.37 (2H, t, J=6.3 Hz), 2.88 (2H, d, J=11.7 Hz), 2.67 (3H, m), 2.36 (2H, t, J=11.7 Hz), 2.31 (2H, s), 1.76 (2H, m), 1.67 (6H, d, J=7.0 Hz), 1.65-1.30 (7H, m). Signals due to C$\underline{H}$(CH$_3$)$_2$ and O$\underline{H}$ was not observed.

Anal. Calcd. for C$_{26}$H$_{37}$N$_3$O$_4$.0.2H$_2$O: C, 68.01; H, 8.21; N, 9.15. Found: C, 67.86; H, 8.31; N, 8.90.

Example 4

N-({1-[(4-HYDROXYTETRAHYDRO-2H-PY-RAN-4-YL)METHYL]PIPERIDIN-4-YL}METHYL)-1-ISOPROPYL-5-METHYL-2-OXO-1,2-DIHYDROQUINOLINE-3-CARBOXAMIDE ETHANEDIOATE

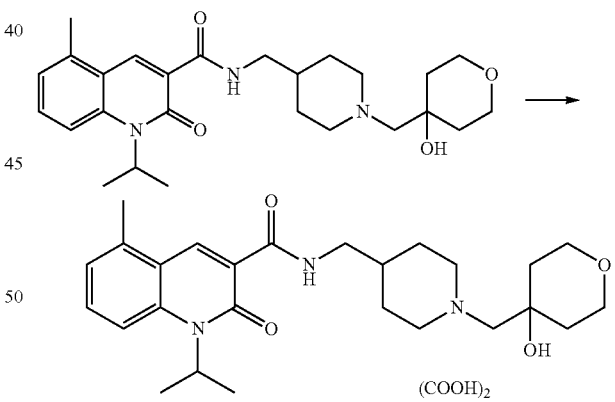

The title compound was prepared according to the procedure of example 2 using N-({1-[(4-hydroxytetrahydro-2H-pyran-4-yl)methyl]piperidin-4-yl}methyl)-1-isopropyl-5-methyl-2-oxo-1,2-dihydroquinoline-3-carboxamide acid (example 3) instead of 5-chloro-N-({1-[(4-hydroxytetrahydro-2H-pyran-4-yl)methyl]piperidin-4-yl}methyl)-1-isopropyl-2-oxo-1,2-dihydroquinoline-3-carboxamide.

MS (ESI) m/z: 456 (M+H$^+$).

m.p.: 222° C.

IR (KBr) ν: 3858, 3820, 3676, 2361, 2341, 1868, 1844, 1830, 1773, 1717, 1653, 1541, 1508, 14889, 1419, 1364, 1221, 1101 cm$^{-1}$.

¹H-NMR (DMSO-d₆) δ: 9.85 (1H, br m), 8.89 (1H, s), 7.73 (1H, d, J=9.0 Hz), 7.61 (1H, dd, J=7.2, 8.8 Hz), 7.22 (1H, d, J=7.2 Hz), 3.59 (4H, m), 3.38 (2H, m), 3.29 (2H, t, J=5.7 Hz), 2.93 (4H, m), 2.61 (3H, s), 1.75 (3H, m), 1.57 (6H, d, J=6.8 Hz), 1.65-1.40 (6H, m). A signal due to OH was not observed.

Anal. Calcd. for $C_{26}H_{37}N_3O_4 \cdot H_2O \cdot 0.2C_6H_{14}O$ (IPE): C, 60.05; H, 7.56; N, 7.19.

Found: C, 60.20; H, 7.46; N, 6.99.

Example 5

5-FLUORO-N-({1-[(4-HYDROXYTETRAHYDRO-2H-PYRAN-4-YL)METHYL]PIPERIDIN-4-YL}METHYL)-1-ISOPROPYL-2-OXO-1,2-DIHYDROQUINOLINE-3-CARBOXAMIDE HYDROCHLORIDE

Step 1. (2-Amino-6-fluorophenyl)methanol

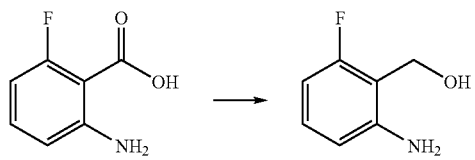

The title compound was prepared according to the procedure of step 1 in the preparation 1 using 2-amino-6-fluorobenzoic acid instead of 2-amino-6-chlorobenzoic acid.

MS (ESI) m/z: 141 (M+H⁺).

¹H-NMR (CDCl₃) δ: 7.08-7.00 (1H, m), 6.48-6.34 (2H, m), 4.78 (2H, s), 4.35 (2H, br). A signal due to OH was not observed.

Step 2. [2-Fluoro-6-(isopropylamino)phenyl]methanol

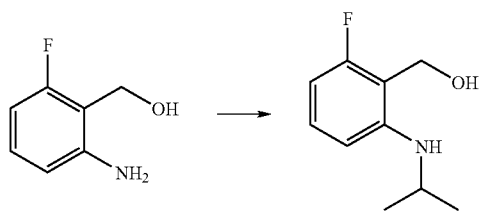

The title compound was prepared according to the procedure of step 2 in the preparation 1 using (2-amino-6-fluorophenyl)methanol (step 1) instead of (2-amino-6-chlorophenyl)methanol.

(The title compound contained 5-fluoro-2,2-dimethyl-1,4-dihydro-2H-3,1-benzoxazine as a by product.)

MS (ESI) m/z: 184 (M+H⁺).

Step 3. 2-Fluoro-6-(isopropylamino)benzaldehyde

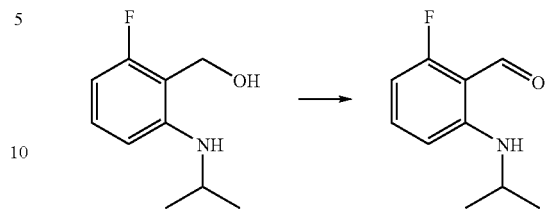

The title compound was prepared according to the procedure of step 3 in the preparation 1 using [2-fluoro-6-(isopropylamino)phenyl]methanol (step 2) instead of [2-chloro-6-(isopropylamino)phenyl]methanol.

¹H-NMR (CDCl₃) δ: 10.25 (1H, s), 8.69 (1H, br s), 7.33-7.25 (1H, m), 6.45 (1H, d, J=8.8 Hz), 6.25-6.18 (1H, m), 3.79-3.68 (1H, m), 1.27 (6H, d, J=6.2 Hz)

Step 4. Ethyl 5-fluoro-1-isopropyl-2-oxo-1,2-dihydroquinoline-3-carboxylate

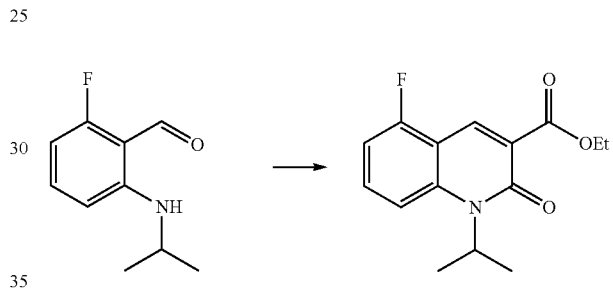

The title compound was prepared according to the procedure of step 1 in alternative route in preparation 2 using 2-fluoro-6-(isopropylamino)benzaldehyde (step 3) instead of 2-(isopropylamino)-6-methylbenzaldehyde.

¹H-NMR (CDCl₃) δ: 8.57 (1H, s), 7.59-7.49 (1H, m), 7.37-7.30 (1H, m), 6.92 (1H, t, J=8.8 Hz), 4.42 (2H, q, J=7.1 Hz), 1.64 (6H, d, J=7.1 Hz), 1.42 (3H, t, J=7.1 Hz). A signal due to CH(CH₃)₂ was not observed.

Step 5. 5-Fluoro-1-isopropyl-2-oxo-1,2-dihydroquinoline-3-carboxylic acid

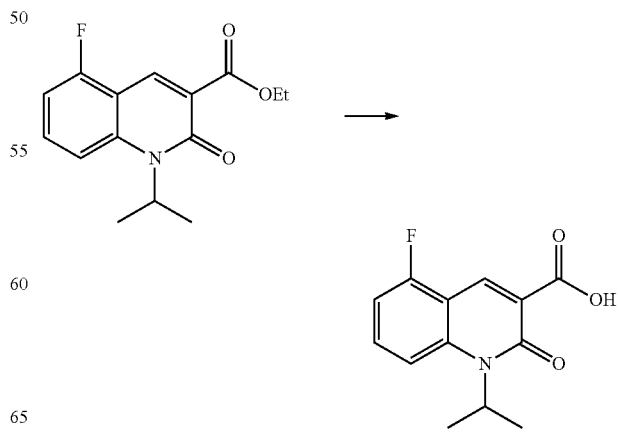

The title compound was prepared according to the procedure of step 2 in alternative route in preparation 2 using ethyl 5-fluoro-1-isopropyl-2-oxo-1,2-dihydroquinoline-3-carboxylate (step 4) instead of ethyl 1-isopropyl-5-methyl-2-oxo-1,2-dihydroquinoline-3-carboxylate.

$^1$H-NMR (CDCl$_3$) δ: 14.53 (1H, s), 9.19 (1H, s), 7.75-7.65 (1H, m), 7.52-7.45 (1H, m), 7.13-7.05 (1H, m), 1.71 (6H, d, J=7.0 Hz). A signal due to CH(CH$_3$)$_2$ was not observed.

Step 6. 5-Fluoro-N-({1-[(4-hydroxytetrahydro-2H-pyran-4-yl)methyl]piperidin-4-yl}methyl)-1-isopropyl-2-oxo-1,2-dihydroquinoline-3-carboxamide hydrochloride

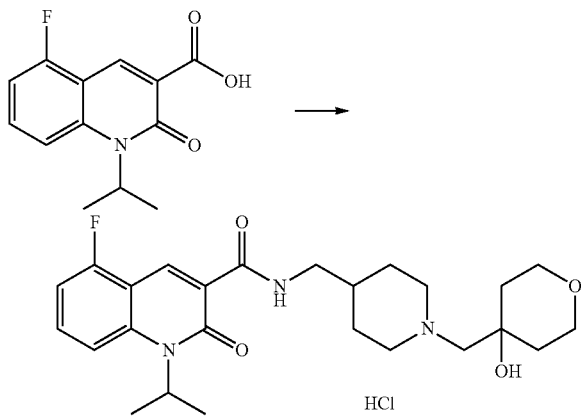

The title compound was prepared according to the procedure of step 3 in the example 1 using 5-fluoro-1-isopropyl-2-oxo-1,2-dihydroquinoline-3-carboxylic acid (step 5) instead of 5-chloro-1-isopropyl-2-oxo-1,2-dihydroquinoline-3-carboxylic acid.

MS (ESI) m/z: 460 (M+H$^+$).
m.p.: 275.7° C.
IR (KBr) ν: 3340, 2947, 2551, 1676, 1614, 1556, 1467, 1380, 1161, 1101, 800 cm$^{-1}$.
$^1$H-NMR (DMSO-d$_6$) δ: 9.83-9.56 (1H, br), 8.81 (1H, s), 7.86-7.61 (2H, m), 7.32-7.11 (1H, m), 5.73 (1H, br s), 5.41-5.23 (5H, m), 3.72-2.89 (9H, m), 1.91-1.41 (14H, m). A signal due to OH was not observed.
Anal. Calcd. for C$_{25}$H$_{35}$N$_3$O$_4$FCl.0.1H$_2$O: C, 60.32; H, 7.13; N, 8.44. Found: C, 59.98; H, 7.20; N, 8.30.

Example 6

1-ISOPROPYL-5-METHYL-2-OXO-N-{[1-(PIPERIDINE-4-YLMETHYL)PIPERIDINE-4-YL]METHYL}-1,2-DIHYDROQUINOLINE-3-CARBOXAMIDE

Step 1. tert-Butyl 4-{[4-({[(1-isopropyl-5-methyl-2-oxo-1,2-dihydroquinolin-3-yl)carbonyl]-amino}methyl)piperidine-1-yl]methyl}piperidine-1-carboxylate

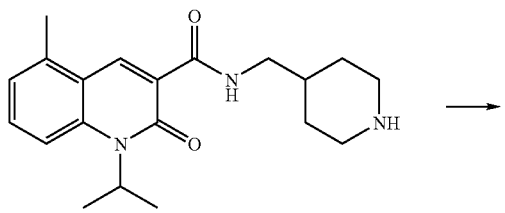

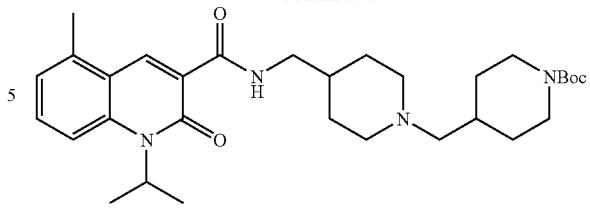

To a solution of 1-isopropyl-5-methyl-2-oxo-N-(piperidin-4-ylmethyl)-1,2-dihydroquinoline-3-carboxamide (300 mg, 0.88 mmol, step 4 in preparation 3) in N,N-dimethylformamide (30 mL), tert-butyl 4-(iodomethyl)piperidine-1-caroxylate (343 mg, 1.05 mmol, Villalobos Anabella et al., J. Med. Chem., 1994, 37, 2721) and potassium carbonate (610 mg, 4.4 mmol) were added at room temperature. The mixture was heated at 80° C. overnight. After cooled to room temperature, water (30 mL) was added and extracted with diethyl ether (50 mL×2). The combined organic layer was washed with water (20 mL×2), brine (20 mL), dried over magnesium sulfate and concentrated in vacuo gave yellow oil, which was chromatographed on a column of silica gel eluting with ethyl 25% ammonium oxide/methanol/dichloromethane (3:30:1000) to give 154 mg (32%) of the title compound as a clear colorless oil.

$^1$H-NMR (CDCl$_3$) δ: 10.07 (1H, br s), 9.11 (1H, s), 7.59-7.44 (2H, m), 7.19-7.07 (1H, m), 5.30 (2H, s), 3.40-3.30 (2H, m), 2.92-2.78 (2H, m), 2.75-2.55 (5H, m), 2.15-2.10 (2H, m), 1.98-1.75 (2H, m), 1.75-1.25 (26H, m).

Step 2. 1-Isopropyl-5-methyl-2-oxo-N-{[1-(piperidin-4-ylmethyl)piperidin-4-yl]methyl}-1,2-dihydroquinoline-3-carboxamide dihydrochloride

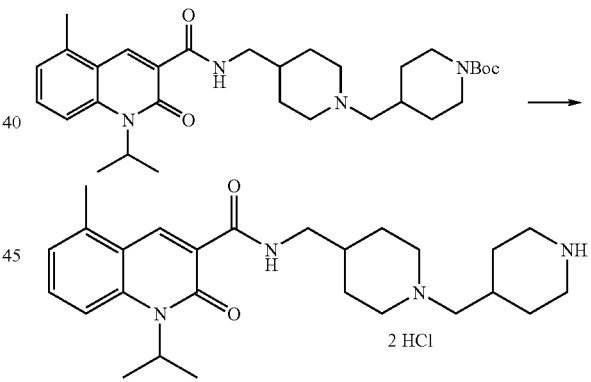

tert-Butyl 4-{[4-({[(1-isopropyl-5-methyl-2-oxo-1,2-dihydroquinolin-3-yl)carbonyl]amino}methyl)piperidine-1-yl]methyl}piperidine-1 carboxylate (150 mg, 0.28 mmol, step 1) was dissolved in 10% methanolic hydrogen chloride (20 mL) and the mixture was stirred for 16 h at room temperature. The mixture was concentrated to give yellow oil, which was crystallized from diethyl ether and n-hexane. The solid was collected by filtration to give 110 mg (96%) of the title compound as a pale yellow solid.

MS (ESI) m/z: 439 (M+H$^+$).
m.p.: 240.7° C.
$^1$H-NMR (CDCl$_3$) δ: 10.0-9.83 (1H, br), 8.90 (1H, s), 7.79-7.70 (1H, m), 7.67-7.57 (1H, m), 7.29-7.20 (1H, m), 3.55-1.25 (32H, m). A signal due to CH(CH$_3$)$_2$ was not observed.
Anal. Calcd. for C$_{26}$H$_{40}$N$_4$O$_2$Cl$_2$.2H$_2$O: C, 57.03; H, 8.10; N, 10.23. Found: C, 56.68; H, 8.25; N, 9.84.

Example 7

N-({1-[(4-HYDROXYPIPERIDIN-4-YL)METHYL]PIPERIDINE-4-YL}METHYL)-1-ISOPROPYL-5-METHYL-2-OXO-1,2-DIHYDROQUINOLINE-3-CARBOXAMIDE ETHANEDIOATE

Step 1. tert-Butyl 4-hydroxy-4-{[4-({[1-isopropyl-5-methyl-2-oxo-1,2-dihydroquinolin-3-yl)carbonyl]amino}methyl)piperidine-1-yl]methyl}piperidine-1-carboxylate

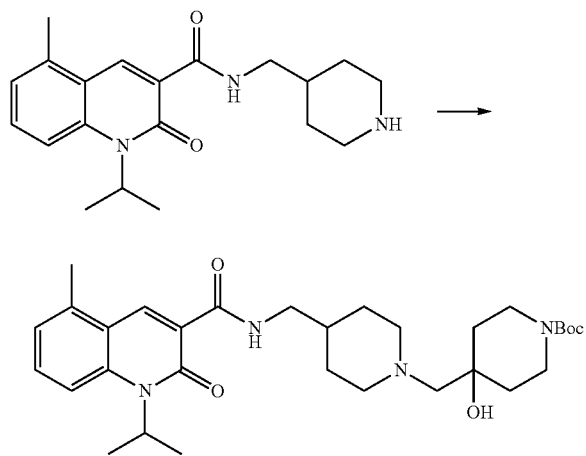

A solution of 1-isopropyl-5-methyl-2-oxo-N-(piperidin-4-ylmethyl)-1,2-dihydroquinoline-3-carboxamide (150 mg, 0.44 mmol, step 4 in preparation 3) and tert-butyl 1-oxa-6-azaspiro[2.5]octane-6-carboxylate (112 mg, 0.53 mmol, Castro Jose L. et al., *J. Med. Chem.,* 1998, 41, 2667) in methanol (5 mL) was heated at 80° C. overnight. After cooled to room temperature, concentrated gave yellow oil. The residue was chromatographed on a column of silica gel eluting with 25% ammonium hydroxide/methanol/dichloromethane (2/10/100) to give 111 mg (45%) of the title compound as a white solid.

$^1$H-NMR (CDCl$_3$) δ: 10.05 (1H, br), 9.25 (1H, s), 7.65-7.41 (2H, m), 7.20-7.10 (1H, m), 3.94-3.74 (1H, m), 3.47-3.28 (2H, m), 2.95-2.81 (2H, m), 2.67 (3H, s), 2.47-2.21 (4H, m), 1.86-1.19 (28H, m). A signal due to OH was not observed.

Step 2. N-({1-[(4-hydroxypiperidin-4-yl)methyl]piperidine-4-yl}methyl)-1-isopropyl-5-methyl-2-oxo-1,2-dihydroquinoline-3-carboxamide ethanedioate

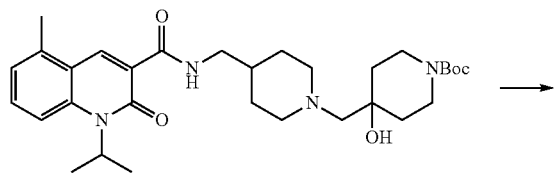

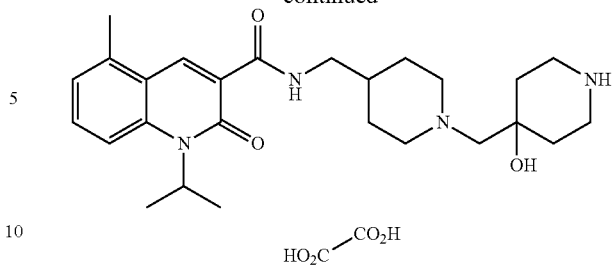

tert-Butyl 4-hydroxy-4-{[4-({[(1-isopropyl-5-methyl-2-oxo-1,2-dihydroquinolin-3-yl)carbonyl]amino}methyl)piperidine-1-yl]methyl}piperidine-1-carboxylate (110 mg, 0.20 mmol) was dissolved in 10% hydrogen chloride in methanol (10 mL) and the mixture was concentrated in vacuo to give a white solid. The solid was suspended in tetrahydrofuran/methanol (4/1, 80 mL) and potassium carbonate (500 mg, 3.6 mmol) was added. The mixture was stirred for 30 min at room temperature, filtered through a pad of Celite, washed with tetrahydrofuran/methanol (4/1, 30 mL), the filtrate was concentrated to give 52 mg of pale yellow oil. The resultant oil was dissolved in methanol (5 mL) and oxalic acid (10 mg, 0.11 mmol) was added. The mixture was stirred for 10 min and concentrated in vacuo gave white solid. The solid was suspended in ethyl acetate and collected by filtration gave 80 mg (74%) of the title compound as a pale yellow solid.

MS (ESI) m/z: 455 (M+H$^+$).

$^1$H-NMR (CDCl$_3$) δ: 9.88 (1H, br), 8.92 (1H, s), 7.79-7.72 (1H, m), 7.68-7.56 (1H, m), 7.28-7.21 (1H, m), 2.65 (3H, s), 3.90-1.30 (28H, m). Signals due to NH (piperidine) and OH were not observed.

Anal. Calcd. for C$_{28}$H$_{40}$N$_4$O$_7$·2.5H$_2$O·1EtOAc: C, 56.71; H, 7.88; N, 8.27. Found: C, 56.77; H, 7.55; N, 8.38.

Example 8

N-({1-[(4-HYDROXY-1-METHYLPIPERIDIN-4-YL)METHYL]PIPERIDIN-4-YL}METHYL)-1-ISOPROPYL-5-METHYL-2-OXO-1,2-DIHYDROQUINOLINE-3-CARBOXAMIDE ETHANEDIOATE

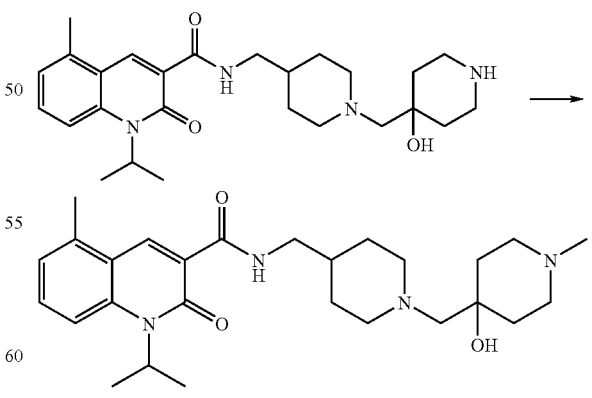

A mixture of N-({1-[(4-hydroxypiperidin-4-yl)methyl]piperidine-4-yl}methyl)-1-isopropyl-5-methyl-2-oxo-1,2-dihydroquinoline-3-carboxamide (100 mg, 0.22 mmol), formaldehyde (37 wt. % solution in water, 1.5 mL) and formic acid (1 mL) was heated at 80° C. overnight. After cooled to room temperature, concentrated in vacuo gave white solid. The resultant solid was added saturated aqueous sodium bicarbonate (15 mL) and concentrated in vacuo, the residual solid was suspended in tetrahydrofuran/methanol (4/1; 60 mL) and stirred for 1 h at room temperature. The mixture was filtered trough a pad of celite, washed with tetrahydrofuran/methanol (4/1; mL), concentrated in vacuo gave white solid. The resultant solid was chromatographed on a column of silica gel eluting with 25% ammonium hydroxide/methanol/dichloromethane (1:5:100) to give 53 mg of clear colorless oil. The resultant oil was dissolved in methanol (5 mL) and oxalic acid (10 mg, 0.11 mmol) was added. After stirring for 10 min, concentrated in vacuo gave white solid, which was washed with ethyl acetate, collected by filtration gave 45 mg (37%) of the title compound as a white powder.

MS (ESI) m/z: 469 (M+H$^+$).

$^1$H-NMR (CDCl$_3$) δ: 9.88 (1H, br), 8.91 (1H, s), 7.78-7.72 (1H, m), 7.68-7.57 (1H, m), 7.28-7.21 (1H, m), 2.75 (3H, s), 2.64 (3H, s), 3.90-1.30 (28H, m). A signal due to OH was not observed.

Anal. Calcd. for C$_{28}$H$_{40}$N$_4$O$_7$2.5H$_2$O.1EtOAc: C, 56.71; H, 7.88; N, 8.27. Found: C, 56.77; H, 7.55; N, 8.38.

Example 9

N-({1-[(cis-1,4-DIHYDROXYCYCLOHEXYL) METHYL]PIPERIDIN-4-YL}METHYL)-1-ISO- PROPYL-5-METHYL-2-OXO-1,2-DIHYDRO- QUINOLINE-3-CARBOXAMIDE ETHANEDIOATE Step 1. tert-Butyl(1-oxaspiro[2.5]oct-6-yloxy)diphenylsilane

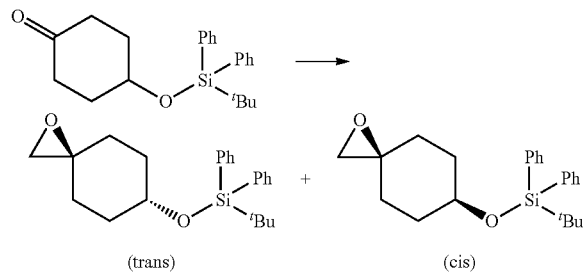

To a stirred suspension of sodium hydride (60% in mineral oil, 441 mg, 11.0 mmol) in dimethylsulfoxide (7 mL) was added trimethylsulfoxonium iodide (2.53 g, 11.5 mmol) at room temperature, and the mixture was stirred at room temperature for 30 min. To this mixture was added a solution of 4-{[tert-butyl(diphenyl)silyl]oxy}cyclohexanone (3.53 g, 10.0 mmol, Okamura, William H. et al., J. Org. Chem., 1993, 58, 600) in dimethylsulfoxide (35 mL) dropwise at room temperature, and the mixture was stirred at room temperature for 2 h. Then the mixture was diluted with water (600 mL), and extracted with diethyl ether (200 mL×4). The combined organic layer was dried over magnesium sulfate, and concentrated in vacuo. The residue was chromatographed on a column of silica gel eluting with ethyl acetate/n-hexane (1:10), and then purified with plate TLC eluting with ethyl acetate/ n-hexane (1:15) to give 459 mg (13%, trans) and 390 mg (11%, cis) of the title compound as a colorless oil respectively.

(trans)

$^1$H-NMR (CDCl$_3$) δ: 7.70-7.66 (4H, m), 7.46-7.35 (6H, m), 4.03-3.97 (1H, m), 2.63 (2H, s), 2.07-1.63 (8H, m), 1.08 (9H, s).

(cis)

$^1$H-NMR (CDCl$_3$) δ: 7.70-7.65 (4H, m), 7.46-7.35 (6H, m), 3.97-3.83 (1H, m), 2.58 (2H, s), 1.83-1.37 (8H, m), 1.07 (9H, s).

Step 2. N-({1-[(cis-4-{[tert-Butyl(diphenyl)silyl] oxy}-1-hydroxycyclohexyl)methyl]piperidin-4- yl}methyl)-1-isopropyl-5-methyl-2-oxo-1,2-dihydro- quinoline-3-carboxamide

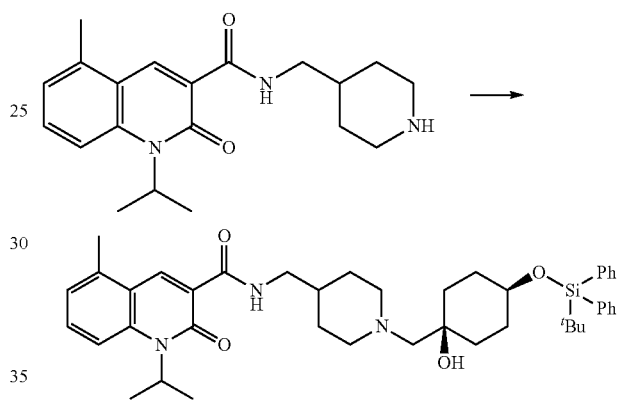

A mixture of 1-isopropyl-5-methyl-2-oxo-N-(piperidin-4- ylmethyl)-1,2-dihydroquinoline-3-carboxamide (346 mg, 1.01 mmol, step 4 in preparation 3) and tert-butyl[(3s,6s)-1- oxaspiro[2.5]oct-6-yloxy]diphenylsilane (390 mg, 1.06 mmol, Step 1, cis-isomer) in methanol (3 mL) was stirred at room temperature for 16 h, and then the solvent was removed in vacuo. The residue was chromatographed on a column of silica gel eluting with methanol/dichloromethane (1:20) to give 682 mg (95%) of the title compound as a colorless oil.

$^1$H-NMR (CDCl$_3$) δ: 10.04 (1H, br), 9.13 (1H, s), 7.70- 7.67 (4H, m), 7.50-7.32 (8H, m), 7.12-7.09 (1H, m), 3.60 (1H, br), 3.38-3.34 (2H, m), 2.86-2.82 (2H, m), 2.66 (3H, s), 2.31- 2.16 (4H, m), 1.84-0.85 (20 h, m), 1.05 (9H, s). A signal due to OH was not observed.

Step 3. N-({1-[(cis-1,4-Dihydroxycyclohexyl)me- thyl]piperidin-4-yl}methyl)-1-isopropyl-5-methyl-2- oxo-1,2-dihydroquinoline-3-carboxamide

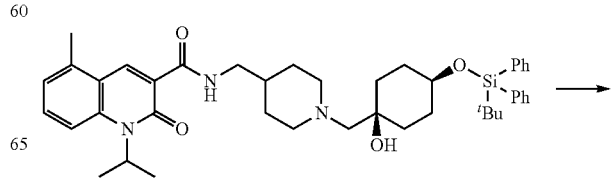

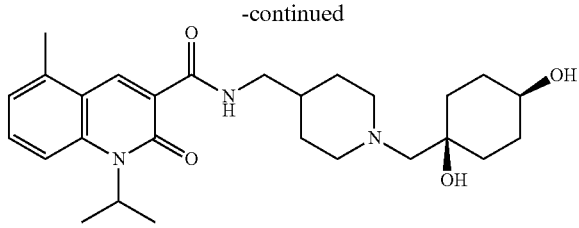

To a stirred solution of N-({1-[(cis-4-{[tert-butyl(diphenyl)silyl]oxy}-1-hydroxycyclohexyl)methyl]piperidin-4-yl}methyl)-1-isopropyl-5-methyl-2-oxo-1,2-dihydroquinoline-3-carboxamide (682 mg, 0.96 mmol, step 2) in tetrahydrofuran (6 mL) was added a solution of tetrabutylammonium fluoride in tetrahydrofuran (1.0M, 2.0 mL, 2.0 mmol) at 0° C., and the mixture was stirred at room temperature for 16 h, then refluxed for 6 h. After cooling to room temperature, the solvent was removed in vacuo. The residue was chromatographed on a column of silica gel eluting with 25% ammonium hydroxide/methanol/dichloromethane (0.2:1:10) to give 295 mg (65%) of the title compound as a white solid.

¹H-NMR (CDCl₃) δ: 10.04 (1H, br), 9.12 (1H, s), 7.50-7.49 (2H, m), 7.13-7.10 (1H, m), 3.60-3.52 (1H, m), 3.41-3.35 (4H, m), 2.91-2.88 (2H, m), 2.66 (3H, s), 2.38-2.28 (4H, m), 1.77-0.98 (18H, m). Signals due to cis-diol (OH×2) were not observed.

Step 4. N-({1-[(cis-1,4-dihydroxycyclohexyl)methyl]piperidin-4-yl}methyl)-1-isopropyl-5-methyl-2-oxo-1,2-dihydroquinoline-3-carboxamide ethanedioate (CJ-044476-13)

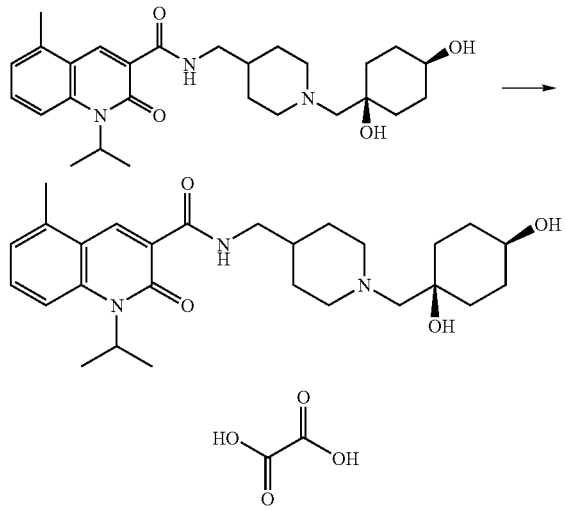

A mixture of N-({1-[(cis-1,4-dihydroxycyclohexyl)methyl]piperidin-4-yl}methyl)-1-isopropyl-5-methyl-2-oxo-1,2-dihydroquinoline-3-carboxamide (295 mg, 0.628 mmol, step 3) and oxalic acid (56.6 mg, 0.628 mmol) was dissolved in methanol and stirred for 1 h. The mixture was concentrated and recrystallized in 2-propanol to give 246 mg (70%) of the title compound as a white solid.

MS (ESI) m/z: 470 (M+H⁺).

m.p.: 226° C. (decomposition).

IR (KBr) ν: 3377, 3277, 2937, 2868, 1753, 1719, 1663, 1589, 1541, 1464, 1448, 1400, 1381, 1302, 1281, 1223, 1151, 1109, 1053, 1032, 972, 800, 719 cm⁻¹.

¹H-NMR (DMSO-d₆) δ: 9.85 (1H, br), 8.89 (1H, s), 7.73 (1H, d, J=8.9 Hz), 7.63-7.57 (1H, m), 7.22 (1H, d, J=7.1 Hz), 3.44-3.26 (6H, m), 3.00-2.84 (5H, m), 2.60 (3H, s), 1.78-1.26 (18H, m). Signals due to cis-diol (OH×2) were not observed.

Anal. Calcd. for C₂₇H₃₉N₃O₄·C₂H₂O₄·1.0H₂O: C, 60.30; H, 7.50; N, 7.27. Found: C, 60.67; H, 7.53; N, 7.17.

Example 10

N-({1-[(trans-1,4-DIHYDROXYCYCLOHEXYL)METHYL]PIPERIDIN-4-YL}METHYL)-1-ISOPROPYL-5-METHYL-2-OXO-1,2-DIHYDROQUINOLINE-3-CARBOXAMIDE ETHANEDIOATE Step 1. N-({1-[(trans-4-{[tert-Butyl(diphenyl)silyl]oxy}-1-hydroxycyclohexyl)methyl]piperidin-4-yl}methyl)-1-isopropyl-5-methyl-2-oxo-1,2-dihydroquinoline-3-carboxamide

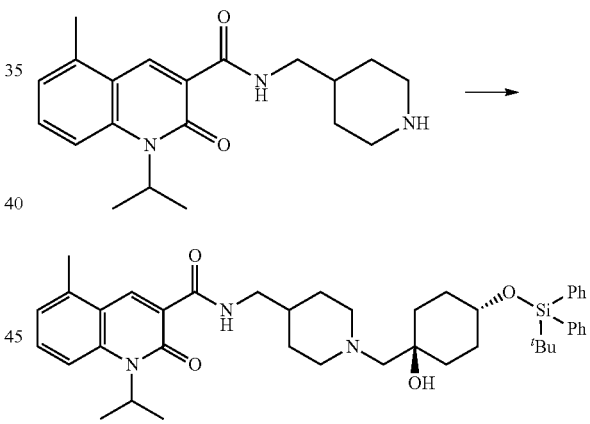

A mixture of 1-isopropyl-5-methyl-2-oxo-N-(piperidin-4-ylmethyl)-1,2-dihydroquinoline-3-carboxamide (156 mg, 0.46 mmol, step 4 in preparation 3) and tert-butyl[(3r,6r)-1-oxaspiro[2.5]oct-6-yloxy]diphenylsilane (176 mg, 0.48 mmol, step 1 in example 9, trans-isomer,) in methanol (2 mL) was stirred at room temperature for 16 h, and then the solvent was removed in vacuo. The residue was chromatographed on a column of silica gel eluting with methanol/dichloromethane (1:20) to give 313 mg (96%) of the title compound as a colorless oil.

¹H-NMR (CDCl₃) δ: 10.05 (1H, br), 9.14 (1H, s), 7.67-7.64 (4H, m), 7.51-7.33 (8H, m), 7.14-7.11 (1H, m), 3.96 (1H, br), 3.40-3.35 (2H, m), 2.94-2.90 (2H, m), 2.68 (3H, s), 2.41-2.33 (4H, m), 1.79-1.29 (20H, m), 1.06 (9H, s). A signal due to OH was not observed.

Step 2. N-({1-[(trans-1,4-Dihydroxycyclohexyl)methyl]piperidin-4-yl}methyl)-1-isopropyl-5-methyl-2-oxo-1,2-dihydroquinoline-3-carboxamide

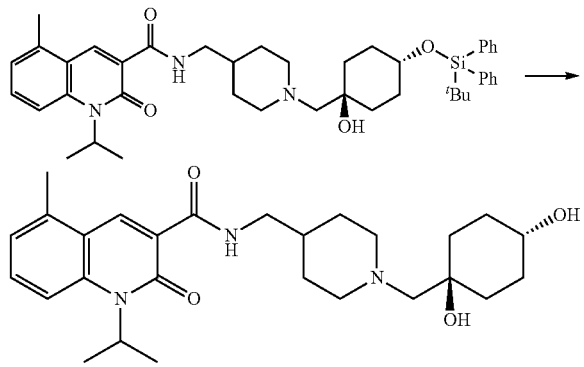

To a stirred solution of N-({1-[(trans-4-{[tert-butyl(diphenyl)silyl]oxy}-1-hydroxycyclohexyl)methyl]piperidin-4-yl}methyl)-1-isopropyl-5-methyl-2-oxo-1,2-dihydroquinoline-3-carboxamide (313 mg, 0.44 mmol, step 1) in tetrahydrofuran (3 mL) was added a solution of tetrabutylammonium fluoride in tetrahydrofuran (1.0 M, 0.9 mL, 0.9 mmol) at 0° C., and the mixture was stirred at room temperature for 16 h, then refluxed for 5 h. After cooling to room temperature, the solvent was removed in vacuo. The residue was purified with plate TLC eluting with methanol/dichloromethane (1:10) to give 192 mg (92%) of the title compound as a slightly yellow amorphous solid.

$^1$H-NMR (CDCl$_3$) δ: 10.02 (1H, br), 9.08 (1H, s), 7.47-7.46 (2H, m), 7.09-7.07 (1H, m), 3.89 (1H, br), 3.35-3.31 (5H, m), 2.90-2.86 (2H, m), 2.63 (3H, s), 2.38-2.29 (4H, m), 1.90-0.81 (17H, m). Signals due to trans-diol (OH×2) were not observed.

Step 3. N-({1-[(trans-1,4-Dihydroxycyclohexyl)methyl]piperidin-4-yl}methyl)-1-isopropyl-5-methyl-2-oxo-1,2-dihydroquinoline-3-carboxamide ethanedioate A mixture of N-({1-[(trans-1,4-dihydroxycyclohexyl)methyl]piperidin-4-yl}methyl)-

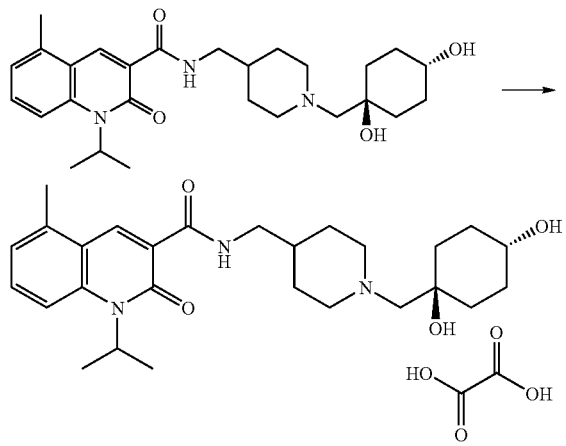

1-isopropyl-5-methyl-2-oxo-1,2-dihydroquinoline-3-carboxamide (192 mg, 0.409 mmol, step 2) and oxalic acid (36.8 mg, 0.409 mmol) was dissolved in methanol and stirred for 1 h. The mixture was concentrated and recrystallized in 2-propanol to give 106 mg (46%) of the title compound as a white solid.

MS (ESI) m/z: 470 (M+H$^+$).
m.p.: 212° C. (decomposition).
IR (KBr) ν: 3568, 3377, 2939, 2870, 1751, 1668, 1605, 1589, 1556, 1464, 1448, 1406, 1379, 1310, 1281, 1221, 1196, 1167, 1151, 1099, 1018, 800, 719 cm$^{-1}$.

$^1$H-NMR (DMSO-d$_6$) δ: 9.85 (1H, br), 8.89 (1H, s), 7.73 (1H, d, J=8.8 Hz), 7.63-7.58 (1H, m), 7.22 (1H, d, J=7.2 Hz), 3.67 (1H, br), 3.45-3.29 (5H, m), 3.04-2.86 (6H, m), 2.61 (3H, s), 1.78-1.29 (17H, m). Signals due to trans-diol (OH×2) were not observed.

Anal. Calcd. for C$_{27}$H$_{39}$N$_3$O$_4$·C$_2$H$_2$O$_4$·0.5H$_2$O: C, 61.25; H, 7.44; N, 7.39. Found: C, 60.90; H, 7.613; N, 7.16.

Example 11

1-ISOPROPYL-5-METHYL-N-{[1-(1-METHYL-2-MORPHOLIN-4-YL-2-OXOETHYL)PIPERIDIN-4-YL]METHYL}-2-OXO-1,2-DIHYDROQUINOLINE-3-CARBOXAMIDE HYDROCHLORIDE

Step 1. tert-Butyl 2-[4-({[(1-isopropyl-5-methyl-2-oxo-1,2-dihydroquinolin-3-yl)carbonyl]amino}methyl)piperidin-1-yl]propanoate

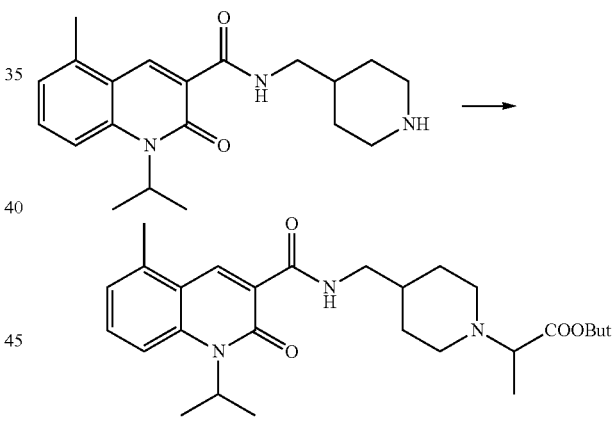

A mixture of 1-isopropyl-5-methyl-2-oxo-N-(piperidin-4-ylmethyl)-1,2-dihydroquinoline-3-carboxamide hydrochloride (467 mg, 0.98 mmol, step 4 in preparation 3), tert-butyl 2-bromopropanoate (0.24 mL, 1.47 mmol), and triethylamine (0.41 mL, 2.93 mmol) in tetrahydrofuran (30 mL) was stirred at 70° C. for 23 h. After cooling to room temperature, the mixture was poured onto saturated aqueous sodium hydrogen carbonate (100 mL), and the aqueous layer was extracted with dichloromethane (100 mL×2). The combined organic layer was dried over magnesium sulfate, and concentrated in vacuo. The residue was chromatographed on a column of silica gel eluting with ammonia/methanol/dichloromethane (0.1:1:30) to give 299 mg (65%) of the title compound as a yellow amorphous.

MS (ESI) m/z: 470 (M+H$^+$).
$^1$H-NMR (DMSO-d$_6$) δ: 10.02 (1H, br), 9.13 (1H, s), 7.53-7.47 (2H, m), 7.12 (1H, t, J=3.6 Hz), 3.38 (2H, t, J=6.3 Hz), 3.18 (1H, q, J=7.1 Hz), 3.03-2.90 (2H, m), 2.67 (3H, s), 2.44-2.20 (2H, m), 1.81 (2H, br d, J=12.5 Hz), 1.68 (6H, d, J=7.1 Hz), 1.46 (9H, s), 1.50-1.25 (3H, m), 1.25 (3H, d, J=7.1 Hz). A signal due to C<u>H</u>(CH₃)₂ was not observed.

Step 2. 2-[4-({[(1-Isopropyl-5-methyl-2-oxo-1,2-dihydroquinolin-3-yl)carbonyl]amino}methyl)piperidin-1-yl]propanoic acid hydrochloride

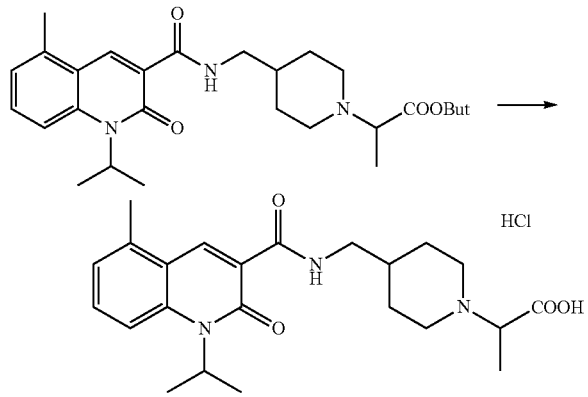

A solution of tert-butyl 2-[4-({[(1-isopropyl-5-methyl-2-oxo-1,2-dihydroquinolin-3-yl)carbonyl]amino}methyl)piperidin-1-yl]propanoate (299 mg, 0.64 mmol, step 1) in trifluoroacetic acid/dichloromethane (1:1, 20 mL) was stirred at room temperature for 16 h. Then, the solvent was removed in vacuo. To the residue was added 10% hydrogen chloride in methanol, and evaporated in vacuo. This was repeated three times to give 295 mg (quant.) of the title compound as a yellow amorphous.

MS (ESI) m/z: 414 (M+H⁺), 412 (M−H⁻).

¹H-NMR (DMSO-d₆) δ: 9.86 (1H, br), 8.89 (1H, s), 7.73 (1H, d, J=8.7 Hz), 9.61 (1H, t, J=7.4 Hz), 7.22 (1H, d, J=7.1 Hz), 3.80-3.25 (7H, m), 2.61 (3H, s), 1.95-1.52 (5H, m), 1.57 (6H, d, J=6.8 Hz), 1.47 (3H, d, J=7.1 Hz). Signals due to C<u>H</u>(CH₃)₂ and CO₂<u>H</u> were not observed.

Step 3. 1-Isopropyl-5-methyl-N-{[1-(1-methyl-2-morpholin-4-yl-2-oxoethyl)piperidin-4-yl]methyl}-2-oxo-1,2-dihydroquinoline-3-carboxamide hydrochloride

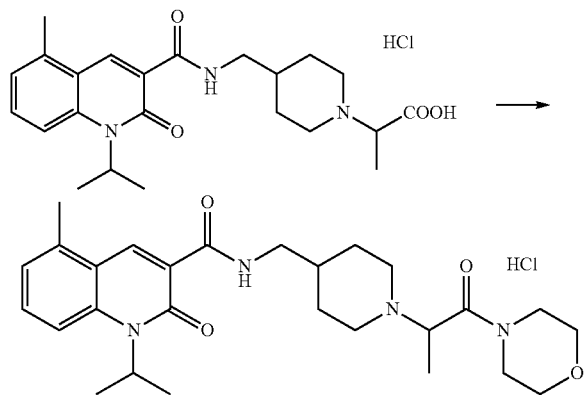

To a mixture of 2-[4-({[(1-isopropyl-5-methyl-2-oxo-1,2-dihydroquinolin-3-yl)carbonyl]amino}methyl)piperidin-1-yl]propanoic acid hydrochloride (243 mg, 0.54 mmol, step 2), morpholine (52 mg, 0.60 mmol), and diisopropylethylamine (0.19 mL, 1.08 mmol) in dichloromethane (15 mL) was added HBTU (226 mg, 0.60 mmol) at 0° C., and the mixture was stirred at 0° C. for 1 h and at room temperature for 3 h. Then, the resulting mixture was poured onto saturated aqueous sodium hydrogen carbonate (100 mL), and the aqueous layer was extracted with dichloromethane (100 mL×3). The combined organic layer was dried over magnesium sulfate, and concentrated in vacuo. The residue was chromatographed on a column of silica gel eluting with ammonia/methanol/dichloromethane (0.1:1:30) to give 265 mg of the title compound as salt free form. This was treated with 10% hydrogen chloride in methanol (5 mL), and the solvent removed in vacuo to give 194 mg (69%) of the title compound as a yellow amorphous.

MS (ESI) m/z: 483 (M+H⁺).

IR (KBr) ν: 3375, 3254, 2930, 2868, 1680, 1655, 1616, 1541, 1464, 1448, 1381, 1238, 1217, 1115, 1034, 953, 800 cm⁻¹.

¹H-NMR (DMSO-d₆) δ: 9.87 (1H, br), 9.59 (1H, br), 8.91 (1H, s), 7.75 (1H, d, J=8.3 Hz), 7.63 (1H, t, J=6.6 Hz), 7.23 (1H, d, J=6.4 Hz), 4.57 (1H, q, J=6.3 Hz), 3.90-2.75 (14H, m), 2.63 (3H, s), 2.00-1.45 (5H, m), 1.59 (6H, d, J=6.3 Hz), 1.07 (3H, d, J=9.6 Hz). A signal due to CH(CH₃)₂ was not observed.

Anal. Calcd. for C₂₇H₃₉ClN₄O₄·1.0MeCN·3.0H₂O: C, 56.71; H, 7.88; N, 11.40.
Found: C, 56.56; H, 7.54; N, 11.45.

Example 12

1-ISOPROPYL-5-METHYL-N-({1-[1-(MORPHOLIN-4-YLCARBONYL)PENTYL]PIPERIDIN-4-YL}METHYL)-2-OXO-1,2-DIHYDROQUINOLINE-3-CARBOXAMIDE HYDROCHLORIDE

Step 1. tert-Butyl 2-[4-({[(1-isopropyl-5-methyl-2-oxo-1,2-dihydroquinolin-3-yl)carbonyl]amino}methyl)piperidin-1-yl]hexanoate

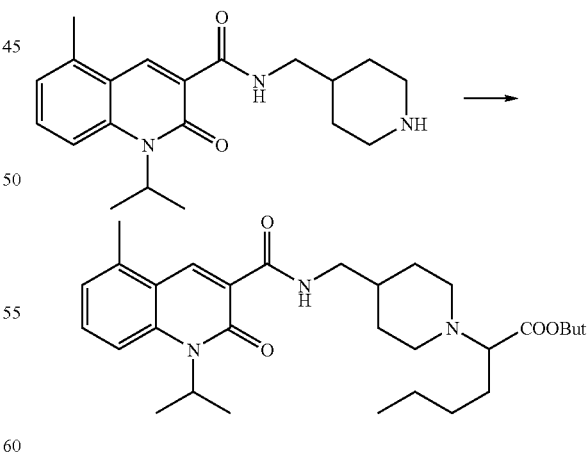

The title compound was prepared according to the procedure of step 1 in the example 11 using tert-butyl 2-bromohexanoate (P. L. Stotter and K. A. Hill, *Tetrahedron Letters*, 1972, 40, 4067.) instead of tert-butyl 2-bromopropanoate.

MS (ESI) m/z: 512 (M+H⁺).

¹H-NMR (CDCl₃) δ: 10.02 (1H, br), 9.13 (1H, s), 7.52-7.47 (2H, m), 7.12 (1H, t, J=4.1 Hz), 4.35 (1H, t, J=7.1 Hz), 3.37 (2H, t, J=6.1 Hz), 2.67 (3H, s), 3.08-2.20 (4H, m), 1.67 (6H, d, J=7.1 Hz), 1.46 (9H, s), 1.85-1.20 (11H, m), 0.89 (3H, t, J=6.6 Hz). A signal due to C$\underline{\text{H}}$(CH$_3$)$_2$ was not observed.

Step 2. 2-[4-({[(1-Isopropyl-5-methyl-2-oxo-1,2-dihydroquinolin-3-yl)carbonyl]amino}methyl)piperidin-1-yl]hexanoic acid hydrochloride

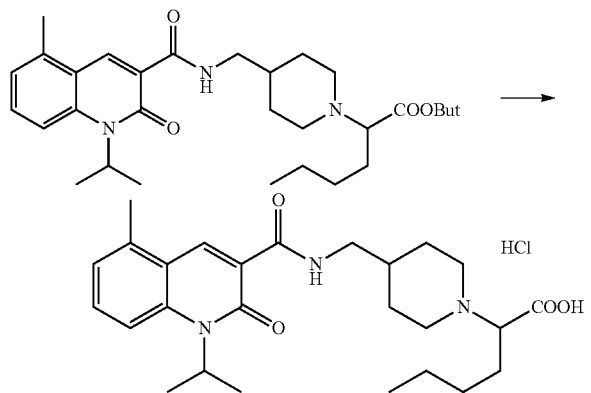

The title compound was prepared according to the procedure of step 2 in the example 11 using tert-butyl 2-[4-({[(1-isopropyl-5-methyl-2-oxo-1,2-dihydroquinolin-3-yl)carbonyl]amino}methyl)piperidin-1-yl]hexanoate (step 1) instead of tert-butyl 2-[4-({[(1-isopropyl-5-methyl-2-oxo-1,2-dihydroquinolin-3-yl)carbonyl]amino}methyl)piperidin-1-yl]propanoate.

MS (ESI) m/z: 414 (M+H$^+$), 412 (M−H$^−$).

$^1$H-NMR (DMSO-d$_6$) δ: 9.85 (1H, br), 8.89 (1H, s), 7.73 (1H, d, J=8.6 Hz), 7.61 (1H, t, J=7.2 Hz), 7.22 (1H, d, J=7.2 Hz), 4.24 (1H, t, J=7.2 Hz), 3.30 (2H, br), 2.61 (3H, s), 2.70-2.05 (4H, m), 1.57 (6H, d, J=7.0 Hz), 1.90-1.20 (11H, m), 0.86 (3H, t, J=6.6 Hz). Signals due to C$\underline{\text{H}}$(CH$_3$)$_2$ and CO$_2$$\underline{\text{H}}$ were not observed.

Step 3. 1-Isopropyl-5-methyl-N-({1-[1-(morpholin-4-ylcarbonyl)pentyl]piperidin-4-yl}methyl)-2-oxo-1,2-dihydroquinoline-3-carboxamide hydrochloride

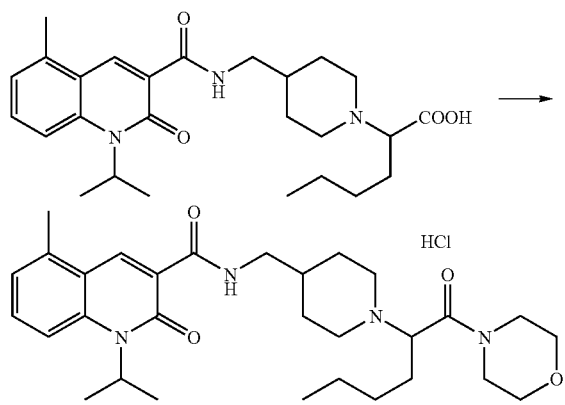

The title compound was prepared according to the procedure of step 3 in the example 11 using 2-[4-({[(1-isopropyl-5-methyl-2-oxo-1,2-dihydroquinolin-3-yl)carbonyl] amino}methyl)piperidin-1-yl]hexanoic acid hydrochloride (step 2) instead of 2-[4-({[(1-isopropyl-5-methyl-2-oxo-1,2-dihydroquinolin-3-yl)carbonyl]amino}methyl)piperidin-1-yl]propanoic acid hydrochloride.

MS (ESI) m/z: 525 (M+H$^+$).

IR (KBr) ν: 2963, 2930, 2866, 1672, 1543, 1448, 1381, 1306, 1261, 1221, 1113, 1069, 1034, 953, 802 cm$^{-1}$.

$^1$H-NMR (DMSO-d$_6$) δ: 9.85 (1H, br), 9.60-9.50 (1H, br), 8.89 (1H, s), 7.73 (1H, d, J=8.8 Hz), 7.61 (1H, t, J=7.3 Hz), 7.22 (1H, d, J=7.2 Hz), 4.55-4.45 (1H, m), 3.75-2.65 (14H, m), 2.61 (3H, s), 1.57 (6H, d, J=6.8 Hz), 1.95-1.10 (11H, m), 0.87 (3H, t, J=7.0 Hz).

Anal. Calcd. for C$_{30}$H$_{45}$ClN$_4$O$_4$·0.5MeCN·2.2H$_2$O: C, 59.93; H, 8.26; N, 10.14. Found: C, 59.75; H, 8.41; N, 10.14.

Preparation 1

N-[(1-BUTYLPIPERIDIN-4-YL)METHYL]-5-CHLORO-1-ISOPROPYL-2-OXO-1,2-DIHYDROQUINOLINE-3-CARBOXAMIDE HYDROCHLORIDE

Step 1. (2-Amino-6-chlorophenyl)methanol

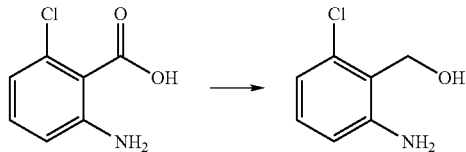

To a suspension of lithium aluminum hydride (1.1 g, 29.1 mmol) in tetrahydrofuran (150 mL) was added 2-amino-6-chlorobenzoic acid (5 g, 29.1 mmol) at 0° C. The mixture was stirred at room temperature for 16 h. Then, the reaction mixture was quenched with sodium sulfate decahydrate (3 g) and brine (10 ml) and filtrated through a pad of Celite. The organic layer was concentrated in vacuo and the residue was chromatographed on a column of silica gel eluting with ethyl acetate/hexane (1:2) to give 2.4 g (52%) of the title compound as a colorless oil.

$^1$H-NMR (CDCl$_3$) δ: 7.01 (1H, dd, J=7.9, 8.1 Hz), 6.76 (1H, d, J=7.9 Hz), 6.58 (1H, d, J=8.1 Hz), 4.88 (2H, s). Signals due to N$\underline{\text{H}}_2$ and O$\underline{\text{H}}$ were not observed.

Step 2.
[2-Chloro-6-(isopropylamino)phenyl]methanol

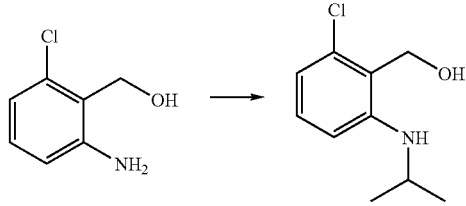

To a mixture of (2-amino-6-chlorophenyl)methanol (2.3 g, 14.6 mmol, step 1), acetic acid (14 mL), sodium acetate hydrate (4.8 g, 58.5 mmol), acetone (7 mL), ethanol (4.8 mL), and water (14 mL) was added a solution of sodium borohydride (1.66 g, 43.9 mmol) in 2N aqueous sodium hydroxide solution (4.8 mL) at 0° C. over a period of 4 h. The mixture was basified with potassium carbonate (3 g) and added water (150 mL). The aqueous layer was extracted with n-hexane. The organic layer was dried over sodium sulfate and concentrated in vacuo to give 2.74 g of the mixture of title compound and 5-chloro-2,2-dimethyl-1,4-dihydro-2H-3,1-benzoxazine (1:1). The mixture was used next reaction without further purification.

$^1$H-NMR (CDCl$_3$) δ: 7.01 (1H, dd, J=8.1, 7.9 Hz), 6.67 (1H, d, J=7.9 Hz), 6.53 (1H, d, J=8.1 Hz), 4.81 (2H, s), 3.64 (1H, m), 1.24 (6H, d, J=6.2 Hz). Signals due to NH and OH were not observed.

Step 3. 2-Chloro-6-(isopropylamino)benzaldehyde

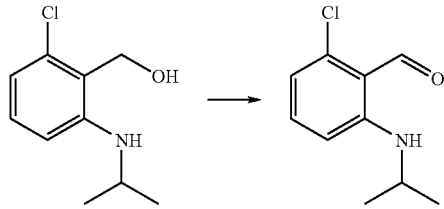

A mixture of [2-chloro-6-(isopropylamino)phenyl]methanol, 5-chloro-2,2-dimethyl-1,4-dihydro-2H-3,1-benzoxazine (2.7 g, ratio; 1:1, step 2) and manganese dioxide (3.9 g, 33.8 mmol) in toluene (50 mL) was stirred at reflux temperature for 16 h. The mixture was filtrated through a pad of Celite and the filtrate was concentrated in vacuo. The residue was chromatographed on a column of silica gel eluting with ethyl acetate/hexane (1:30) to give 1.2 g (45% from (2-amino-6-chlorophenyl)methanol) of the title compound as a yellow solid.

MS (ESI) m/z: 198 (M+H$^+$).

$^1$H-NMR (CDCl$_3$) δ: 10.44 (1H, s), 9.03 (1H, br s), 7.22 (1H, dd, J=7.7, 8.8 Hz), 6.62 (1H, d, J=8.8 Hz), 6.57 (1H, d, J=7.7 Hz), 3.74 (1H, m), 1.26 (6H, d, J=6.2 Hz).

Step 4. 5-Chloro-1-isopropyl-2-oxo-1,2-dihydroquinoline-3-carboxylic acid

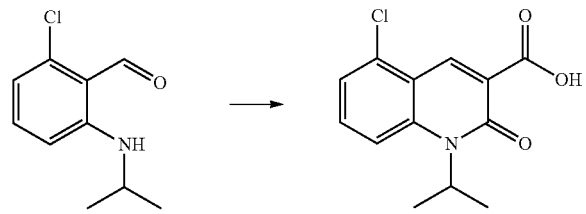

To a solution of 2-chloro-6-(isopropylamino)benzaldehyde (1.1 g, 5.57 mmol, step 3) in methanol (10 mL) was added ethylenediamine (0.186 mL, 2.78 mmol) and acetic acid (0.319 mL, 5.57 mmol). Meldrum's acid (1.6 g, 11.1 mmol) was added to the mixture at 0° C. Then, the mixture was stirred at room temperature for 16 h. The formed precipitate was filtrated and washed with methanol. The filtrate was evaporated and crystallized from methanol to give 200 mg (14%) of the title compound as a white solid.

MS (ESI) m/z: 266 (M+H$^+$).

$^1$H-NMR (DMSO-d$_6$) δ: 8.96 (1H, s), 8.02 (1H, d, J=8.8 Hz), 7.83 (1H, dd, J=8.1, 8.6 Hz), 7.64 (1H, d, J=7.9 Hz), 1.61 (6H, d, J=6.8 Hz). Signals due to CO$_2$H and CH(CH3)$_2$ were not observed.

Step 5. N-[(1-Butylpiperidin-4-yl)methyl]-5-chloro-1-isopropyl-2-oxo-1,2-dihydroquinoline-3-carboxamide hydrochloride

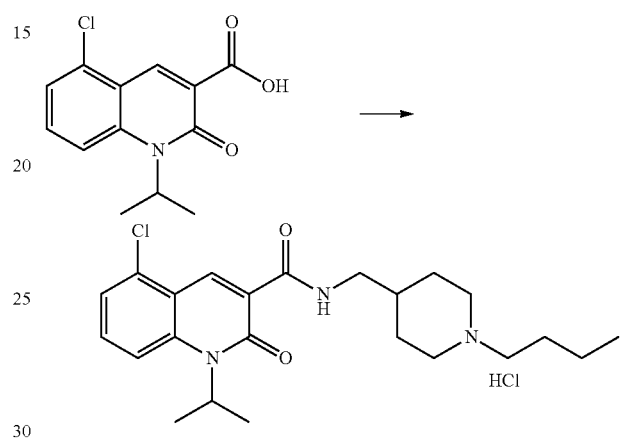

To a solution of 5-chloro-1-isopropyl-2-oxo-1,2-dihydroquinoline-3-carboxylic acid (100 mg, 0.376 mmol, step 4) in dichloromethane (1 mL) was added oxalyl chloride (0.10 mL, 1.13 mmol) and a drop of N,N-dimethylformamide at 0° C. The mixture was stirred at room temperature for 1.5 h. The solvent and excess amount of oxalyl chloride was removed in vacuo. The residue was dissolved in dichloromethane (1 mL) and [(1-butylpiperidin-4-yl)methyl]amine (128 mg, 0.753 mmol) in dichloromethane (1 mL) was added at 0° C. and the mixture was stirred at room temperature for 1 h. Then, the mixture was quenched with water (10 mL) and the aqueous layer was extracted with dichloromethane (20 mL×2). The organic layer was dried over sodium sulfate and concentrated in vacuo gave a colorless oil. The resultant oil was dissolved in 10% methanolic hydrogen chloride (5 mL) and stirred for 16 h. The formed precipitate was filtrated and washed with methanol to give 100 mg (59%) of the title compound as a white solid.

MS (ESI) m/z: 418 (M+H$^+$).

m.p.: 248° C.

IR (KBr) n: 2964, 2935, 2873, 2515, 1678, 1618, 1551, 1445, 1375, 1278, 1207, 1136, 1003 cm$^{-1}$.

$^1$H-NMR (DMSO-d$_6$) δ: 9.74 (1H, t, J=5.9 Hz), 9.03 (1H, s), 7.92 (1H, d, J=9.1 Hz), 7.74 (1H, dd, J=7.9, 8.7 Hz), 7.55 (1H, d, J=7.6 Hz), 3.50-3.15 (6H, br m), 3.00-2.80 (2H, m), 1.90-1.50 (7H, m), 1.60 (6H, d, J=6.9 Hz), 1.31 (2H, m), 0.91 (3H, t, J=7.3 Hz). A signal due to CH(CH3)$_2$ was not observed.

Anal. Calcd. for C$_{23}$H$_{33}$N$_3$O$_2$Cl$_2$: C, 60.79; H, 7.32; N, 9.25. Found: C, 61.08; H, 7.68; N, 9.06.

Preparation 2

N-[(1-BUTYLPIPERIDIN-4-YL)METHYL]-1-ISO-PROPYL-5-METHYL-2-OXO-1,2-DIHYDRO-QUINOLINE-3-CARBOXAMIDE HYDROCHLORIDE

Step 1. (2-Amino-6-methylphenyl)methanol

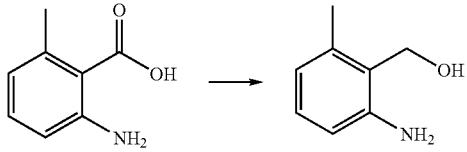

The title compound was prepared according to the procedure of step 1 in the preparation 1 using 2-amino-6-methylbenzoic acid instead of 2-amino-6-chlorobenzoic acid.

$^1$H-NMR (CDCl$_3$) δ: 7.01 (1H, dd, J=7.7 Hz), 6.60 (1H, d, J=7.7 Hz), 6.58 (1H, d, J=7.7 Hz), 4.75 (2H, s), 2.35 (3H, s). Signals due to NH$_2$ and OH were not observed.

Step 2. [2-(Isopropylamino)-6-methylphenyl]methanol

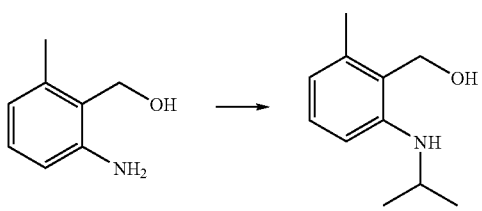

The title compound was prepared according to the procedure of step 2 in the preparation 1 using (2-amino-6-methylphenyl)methanol (step 1) instead of (2-amino-6-chlorophenyl)methanol.

$^1$H-NMR (CDCl$_3$) δ: 7.09 (1H, dd, J=8.1, 7.9 Hz), 6.58 (1H, d, J=8.1 Hz), 6.52 (1H, d, J=7.5 Hz), 4.72 (2H, s), 3.64 (1H, m), 2.35 (3H, s), 1.23 (6H, d, J=6.2 Hz). Signals due to NH and OH were not observed.

Step 3. 2-(Isopropylamino)-6-methylbenzaldehyde

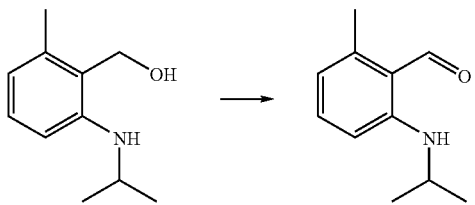

The title compound was prepared according to the procedure of step 3 in the preparation 1 using [2-(isopropylamino)-6-methylphenyl]methanol (step 2) instead of [2-chloro-6-(isopropylamino)phenyl]methanol.

MS (ESI) m/z: 178 (M+H$^+$).

$^1$H-NMR (CDCl$_3$) δ: 10.30 (1H, s), 9.00 (1H, br s), 7.23 (1H, dd, J=8.6, 7.3 Hz), 6.59 (1H, d, J=8.8 Hz), 6.35 (1H, d, J=7.2 Hz), 3.74 (1H, m), 2.55 (3H, s), 1.27 (6H, d, J=6.2 Hz).

Step 4. 1-Isopropyl-5-methyl-2-oxo-1,2-dihydroquinoline-3-carboxylic acid

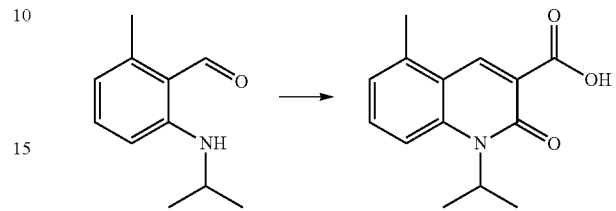

The title compound was prepared according to the procedure of step 4 in the preparation 1 using 2-(isopropylamino)-6-methylbenzaldehyde (step 3) instead of 2-chloro-6-(isopropylamino)benzaldehyde.

MS (ESI) m/z: 246 (M+H$^+$), 244 (M−H$^−$).

$^1$H-NMR (CDCl$_3$) δ: 14.92 (1H, s), 9.14 (1H, s), 7.66-7.55 (2H, m), 7.25-7.18 (1H, m), 2.69 (3H, s), 1.70 (6H, d, J=6.6 Hz). A signal due to CO$_2$H was not observed.

Step 5. N-[(1-Butylpiperidin-4-yl)methyl]-1-isopropyl-5-methyl-2-oxo-1,2-dihydroquinoline-3-carboxamide hydrochloride

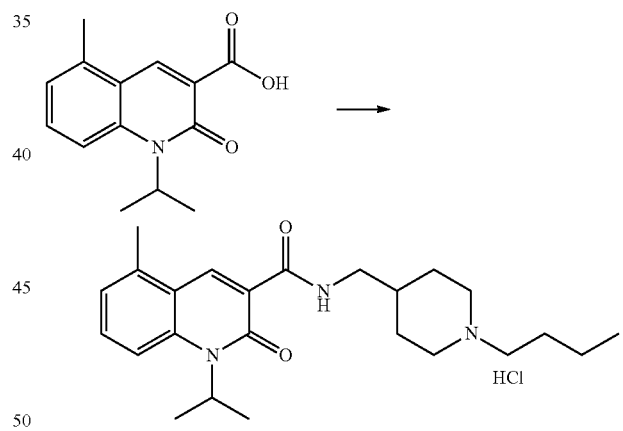

The title compound was prepared according to the procedure of step 5 in the preparation 1 using 1-isopropyl-5-methyl-2-oxo-1,2-dihydroquinoline-3-carboxylic acid (step 4) instead of 5-chloro-1-isopropyl-2-oxo-1,2-dihydroquinoline-3-carboxylic acid.

MS (ESI) m/z: 398 (M+H$^+$).

m.p.: 233° C.

IR (KBr) ν: 3242, 2931, 2876, 2642, 2534, 1684, 1616, 1553, 1466, 1379, 1310, 1217, 1119, 951, 799, 785 cm$^{-1}$.

$^1$H-NMR (DMSO-d$_6$) δ: 9.85 (1H, br m), 8.89 (1H, s), 7.73 (1H, d, J=8.81 Hz), 7.61 (1H, dd, J=7.3, 8.8 Hz), 7.22 (1H, d, J=7.2 Hz), 3.47 (2H, br m), 3.28 (2H, m), 2.95 (2H, m), 2.82 (2H, m), 2.61 (3H, s), 1.81 (3H, m), 1.67-1.45 (4H, m), 1.57 (6H, d, J=7.0 Hz), 1.28 (2H, m), 0.88 (3H, t, J=7.3 Hz). A signal due to CH(CH$_3$)$_2$ was not observed.

Anal. Calcd. for $C_{24}H_{36}N_3O_2Cl_2 \cdot H_2O \cdot 0.2C_6H_{14}O$ (diisopropyl ether): C, 64.06; H, 8.70; N, 8.89. Found: C, 64.45; H, 8.54; N, 9.07.

Alternative route to 1-isopropyl-5-methyl-2-oxo-1,2-dihydroquinoline-3-carboxylic acid (in step 4)

Step 1. Ethyl 1-isopropyl-5-methyl-2-oxo-1,2-dihydroquinoline-3-carboxylate

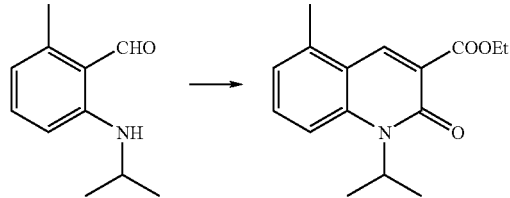

A mixture of 2-(isopropylamino)-6-methylbenzaldehyde (22.4 g, 127 mmol, step 2 in preparation 2), diethyl malonate (22.3 g, 139 mmol), piperidine (1.29 g, 15.2 mmol), and benzoic acid (572 mg, 4.7 mmol) in benzene (500 mL) was refluxed with stirring for 4 days. After cooling to room temperature, the solvent was removed in vacuo. The residue was chromatographed on a column of silica gel eluting with ethyl acetate/hexane (1:15~1:2) to give 19.6 g (57%) of the title compound as a yellow solid.

MS (ESI) m/z: 274 (M+H$^+$).

$^1$H-NMR (CDCl$_3$) δ: 8.57 (1H, s), 7.52-7.41 (2H, m), 7.08-7.03 (1H, m), 4.43 (2H, q, J=7.1 Hz), 2.61 (3H, s), 1.64 (6H, d, J=7.1 Hz), 1.42 (3H, t, J=7.1 Hz). A signal due to CH(CH$_3$)$_2$ was not observed.

Step 2. 1-Isopropyl-5-methyl-2-oxo-1,2-dihydroquinoline-3-carboxylic acid

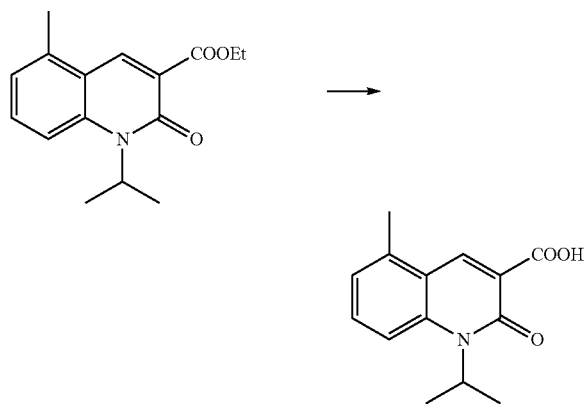

A mixture of ethyl 1-isopropyl-5-methyl-2-oxo-1,2-dihydroquinoline-3-carboxylate (15.0 g, 54.9 mmol), 2N aqueous sodium hydroxide (41 mL, 82 mmol), and ethanol (150 mL) was stirred at room temperature for 2 h. Then, 2N aqueous hydrochloride (41 mL, 82 mmol) was added, and the white precipitate was collected by filtration. This solid was washed with water to give 12.6 g (93%) of the title compound as a pale yellow solid.

MS (ESI) m/z: 246 (M+H$^+$), 244 (M–H$^-$).

$^1$H-NMR (CDCl$_3$) δ: 14.92 (1H, s), 9.14 (1H, s), 7.66-7.55 (2H, m), 7.25-7.18 (1H, m), 2.69 (3H, s), 1.70 (6H, d, J=6.6 Hz). A signal due to CH(CH$_3$)$_2$ was not observed.

Preparation 3

N-({1-[1-(4-HYDROXYTETRAHYDRO-2H-PYRAN-4-YL)ETHYL]PIPERIDIN-4-YL}METHYL)-1-ISOPROPYL-5-METHYL-2-OXO-1,2-DIHYDROQUINOLINE-3-CARBOXAMIDE

Step 1. 4-Ethylidenetetrahydro-2H-pyran

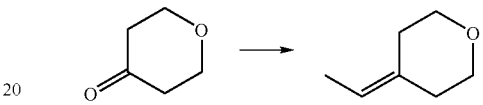

To a suspension of (ethyl)triphenylphosphonium bromide (1.22 g, 3.30 mmol) in diethyl ether (25 mL) was added dropwise a solution of n-butyl lithium in hexane (1.56 M, 2.1 mL, 3.3 mmol) at 0° C., and the mixture was stirred at 0° C. for 20 min. Then, a solution of tetrahydro-4H-pyran-4-one (300 mg, 2.99 mmol) in diethyl ether (5 mL) was added dropwise at 0° C., and the resulting mixture was stirred at room temperature for 4.5 h. Then, the mixture was poured onto water (50 mL), and the aqueous layer was extracted with diethyl ether (100 mL×2). The combined organic layer was dried over sodium sulfate, and concentrated in vacuo. The residue was suspended in hexane, and the insoluble matter was removed by filtration. The filtrate was concentrated in vacuo to give about 500 mg of the title compound as a colorless oil. This was used for the next step without purification.

$^1$H-NMR (CDCl$_3$) δ: 5.30-5.20 (1H, m), 3.69-3.63 (4H, m), 2.27 (2H, t, J=5.7 Hz), 2.20 (2H, br t, J=5.9 Hz), 1.59 (3H, d, J=6.8 Hz).

Step 2. 2-Methyl-1,6-dioxaspiro[2.5]octane

A mixture of 4-ethylidenetetrahydro-2H-pyran (about 500 mg, step 1) and 3-chloroperoxybenzoic acid (1.11 g, 4.49 mmol) in dichloromethane (50 mL) was stirred at 0° C. to room temperature for 1 h. Then, saturated aqueous sodium hydrogen carbonate solution (50 mL) and saturated aqueous sodium thiosulfate solution (50 mL) were added, and the aqueous layer was extracted with dichloromethane (100 mL×3). The combined organic layer was dried over magnesium sulfate, and concentrated in vacuo to give 337 mg of the crude title compound as a yellow oil. This was used for the next step without further purification.

$^1$H-NMR (CDCl$_3$) δ: 3.88-3.75 (4H, m), 2.92 (1H, q, J=5.6 Hz), 1.95-1.80 (2H, m), 1.65-1.40 (2H, m), 1.30 (3H, d, J=5.4 Hz).

Rf: 0.6 (ethyl acetate/hexane=1:1).

Step 3. tert-Butyl 4-({[(1-isopropyl-5-methyl-2-oxo-1,2-dihydroquinolin-3-yl)carbonyl]amino}methyl)piperidine-1-carboxylate

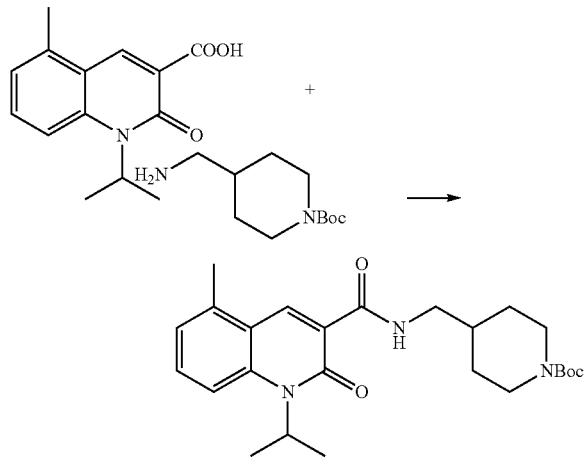

To a solution of 1-isopropyl-5-methyl-2-oxo-1,2-dihydroquinoline-3-carboxylic acid (8.00 g, 32.6 mmol, step 4 in preparation 2) in dichloromethane (200 mL) was added dropwise oxalyl chloride (8.5 mL, 98 mmol) at 0° C. Then, N,N-dimethylformamide (3 drops) was carefully added to the mixture. The resulting mixture was stirred at 0° C. for 30 min and at room temperature for 3 h. Then, the mixture was evaporated in vacuo to give crude acid chloride as a yellow solid. Then, to a mixture of tert-butyl 4-(aminomethyl)piperidine-1-carboxylate (9.08 g, 42.4 mmol) and diisopropylethylamine (11.4 mL, 65.2 mmol) in dichloromethane (200 mL) was added dropwise a solution of crude acid chloride in dichloromethane (50 mL) at 0° C., and the mixture was stirred at room temperature for 3 h. The resulting mixture was poured onto water (300 mL), and the aqueous layer was extracted with dichloromethane (200 mL×3). The combined organic layer was dried over magnesium sulfate, and concentrated in vacuo. The residue was chromatographed on a column of silica gel with ethyl acetate/hexane (1/1.5) and then methanol/dichloromethane (1/40~1/10) to give 15.0 g (quant.) of the title compound as a pale yellow solid.

MS (EI) m/z: 442 (M+H⁺).

¹H-NMR (CDCl₃) δ: 10.07 (1H, br), 9.13 (1H, s), 7.53-7.47 (2H, m), 7.13 (1H, t, J=3.6 Hz), 4.20-4.06 (2H, m), 3.39 (2H, t, J=6.3 Hz), 2.78-2.66 (2H, m), 2.68 (3H, s), 1.67 (6H, d, J=7.1 Hz), 1.45 (9H, s), 1.85-1.18 (5H, m). A signal due to C$\underline{H}$(CH₃)₂ was not observed.

Step 4. 1-Isopropyl-5-methyl-2-oxo-N-(piperidin-4-ylmethyl)-1,2-dihydroquinoline-3-carboxamide

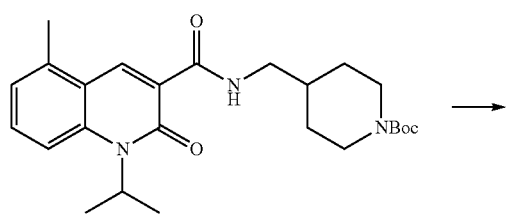

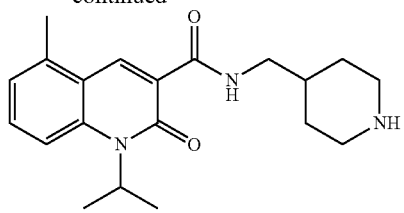

A solution of tert-butyl 4-({[(1-isopropyl-5-methyl-2-oxo-1,2-dihydroquinolin-3-yl)carbonyl]amino}methyl)piperidine-1-carboxylate (15.0 g, 32.6 mmol, step 3) in 10% hydrogen chloride in methanol was stirred at room temperature for 12 h. Then, the solvent was removed in vacuo to give the title compound as hydrochloride salt. This salt was poured onto saturated aqueous sodium hydrogen carbonate solution (500 mL), and the aqueous layer was extracted with dichloromethane (500 mL×5). The combined organic layer was dried over magnesium sulfate and sodium sulfate, and concentrated in vacuo. The residue was chromatographed on a column of aminopropyl silica gel eluting with methanol/dichloromethane (1:10) to give 10.3 g (92%) of the title compound as a pale yellow amorphous.

MS (ESI) m/z: 342 (M+H⁺).

¹H-NMR (CDCl₃) δ: 10.04 (1H, br), 9.13 (1H, s), 7.55-7.42 (2H, m), 7.12 (1H, t, J=4.1 Hz), 3.38 (2H, t, J=6.3 Hz), 3.10 (2H, br d, J=11.9 Hz), 2.68 (3H, s), 2.67-2.55 (2H, m), 1.85-1.60 (3H, m), 1.67 (6H, d, J=7.1 Hz), 1.35-1.15 (2H, m). Signals due to C$\underline{H}$(CH₃)₂ and N$\underline{H}$ (piperidine) were not observed.

Step 5. N-({1-[1-(4-Hydroxytetrahydro-2H-pyran-4-yl)ethyl]piperidin-4-yl}methyl)-1-isopropyl-5-methyl-2-oxo-1,2-dihydroquinoline-3-carboxamide hydrochloride

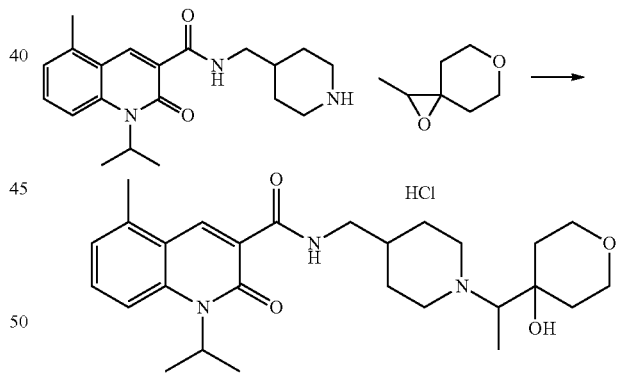

A solution of 1-isopropyl-5-methyl-2-oxo-N-(piperidin-4-ylmethyl)-1,2-dihydroquinoline-3-carboxamide (200 mg, 0.59 mmol, step 4) and 2-methyl-1,6-dioxaspiro[2.5]octane (crude, 2.99 mmol, step 2) in methanol was stirred in a sealed tube at 130° C. for 30 h. After cooling to room temperature, water (100 mL) was added, and the aqueous layer was extracted with dichloromethane (100 mL×3). The combined organic layer was dried over magnesium sulfate, and concentrated in vacuo. The residue was chromatographed on a column of silica gel eluting with ammonia/methanol/dichloromethane (0.1:1:15) to give 180 mg of crude product. This was chromatographed on a column of aminopropyl silica gel eluting with ethyl acetate/hexane (1:1.5) to give 51 mg of the title compound as a salt free form. This was treated with 10% hydrogen chloride in methanol, and the solvent was removed in vacuo to give 35 mg (12%) of the title compound as a white amorphous.

MS (ESI) m/z: 470 (M+H$^+$).

IR (KBr) ν: 3225, 2957, 2866, 2702, 1678, 1616, 1587, 1541, 1464, 1385, 1310, 1217, 1157, 1101, 968, 950, 799 cm$^{-1}$.

$^1$H-NMR (DMSO-d$_6$) δ: 9.85 (1H, m), 8.89 (1H, s), 7.76 (1H, d, J=8.9 Hz), 7.62 (1H, t, J=7.3 Hz), 7.22 (1H, d, J=7.3 Hz), 5.47 (1H, m), 3.80-3.15 (11H, m), 2.61 (3H, s), 2.00-1.25 (9H, m), 1.57 (6H, d, J=6.8 Hz), 1.23 (3H, d, J=6.9 Hz). A signal due to OH was not observed.

Anal. Calcd. for C$_{27}$H$_{40}$ClN$_3$O$_4$·0.2iPr$_2$O·0.7H$_2$O: C, 62.82; H, 8.26; N, 7.79. Found: C, 62.72; H, 7.95; N, 7.50.

The invention claimed is:

1. A compound of the formula (I):

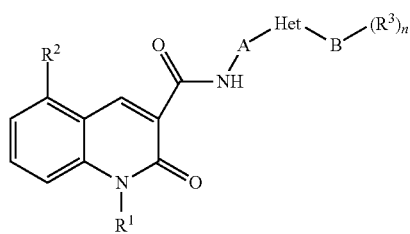

wherein

Het represents a heterocyclic group having one nitrogen atom, to which B binds directly to said nitrogen atom, and from 4 to 7 carbon atoms, and said heterocyclic group being unsubstituted or substituted by 1 to 4 substituents independently selected from the group consisting of substituents α$^1$;

A represents an alkylene group having from 1 to 4 carbon atoms;

B represents a methylene group;

R$^1$ represents an isopropyl group, an n-propyl group or a cyclopentyl group;

R$^2$ represents a methyl group;

R$^3$ independently represents 1,4-dihydroxycyclohexyl or hydroxytetrahydropyranyl;

said substituents α$^1$ are independently selected from the group consisting of a hydroxyl group an amino group; and n is 1;

or a pharmaceutically acceptable salt thereof.

2. The compound or its pharmaceutically acceptable salt of claim 1, wherein:

Het represents a heterocyclic group selected from the group consisting of

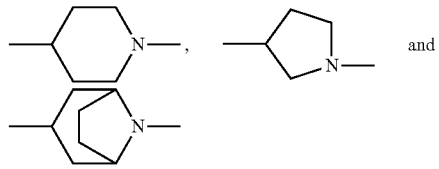

said heterocyclic group being unsubstituted or substituted by 1 to 3 substituents independently selected from the group consisting of substituents α$^1$.

3. The compound or its pharmaceutically acceptable salt of claim 1, wherein:

Het represents a group of formula:

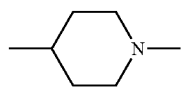

and this group being unsubstituted or substituted by one substituent selected from the group consisting of substituents a';

A represents an alkylene group having from 1 to 3 carbon atoms; and

R$^1$ represents an isopropyl group or a cyclopentyl group.

4. A compound selected from the group consisting of:

N-({1-[(cis-1,4-dihydroxycyclohexyl)methyl]piperidin-4-yl}methyl)-1-isopropyl-5-methyl-2-oxo-1,2-dihydrominoline-3-carboxamide ethanedioate; and N-({1-[(trans-1,4-dihydroxycyclohexyl)methyl]piperidin-4-yl}methyl)-1-isopropyl-5-methyl-2-oxo-1,2-dihydroquinoline-3-carboxamide ethanedioate; or a pharmaceutically acceptable salt thereof.

* * * * *